United States Patent [19]

Haynes

[11] Patent Number: 4,700,294
[45] Date of Patent: Oct. 13, 1987

[54] DATA STORAGE SYSTEM HAVING MEANS FOR COMPRESSING INPUT DATA FROM SETS OF CORRELATED PARAMETERS

[75] Inventor: John L. Haynes, Chapel Hill, N.C.

[73] Assignee: Becton Dickinson and Company, Paramus, N.J.

[21] Appl. No.: 666,300

[22] Filed: Oct. 30, 1984

Related U.S. Application Data

[63] Continuation-in-part of Ser. No. 434,623, Oct. 15, 1982, abandoned.

[51] Int. Cl.⁴ .......................... G06F 7/00; G06F 12/00
[52] U.S. Cl. .................................... 364/200; 364/728; 364/300
[58] Field of Search ... 364/200 MS File, 900 MS File, 364/300, 728, 413

[56] References Cited

U.S. PATENT DOCUMENTS

| | | | |
|---|---|---|---|
| 4,068,298 | 1/1978 | Dechant et al. | 364/200 |
| 4,121,286 | 10/1978 | Venton et al. | 364/200 |
| 4,290,115 | 9/1981 | Pitt et al. | 364/900 |
| 4,354,225 | 10/1982 | Frieder et al. | 364/200 |

Primary Examiner—Raulfe B. Zache
Assistant Examiner—William G. Niessen
Attorney, Agent, or Firm—Fitch, Even, Tabin & Flannery

[57] ABSTRACT

A data storage system utilizing a technique for compressing input data from cross-correlated sets of parameter values. The system dynamically allocates storage space based upon values of the input data. In systems where the multivalues parameters are grouped about a mean value, the data allocation techniques saves considerable memory area over a memory allocation for all possible values. A first embodiment uses one or more pointer matrix memories which store the addresses of blocks of counter locations. The first occurrence of a parameter set causes the assignment of a counter location for that set in a memory block whose address is stored in a pointer called by the occurrence of the set. Upon each subsequent occurrence of a set, the assigned counter location for the set is called through the pointer and incremented to maintain an accurate account of the frequency of the set occurrence. In an alternate embodiment, an encoding technique is utilized to embed address jump and occurrence count data in a single memory space. A data base is reduced by storing the count value of a particular parameter set in one memory location and associating with that location an address increment indicating the distance to the next parameter set. If the next parameter set is a predetermined distance away, then no address increment need be stored.

15 Claims, 27 Drawing Figures

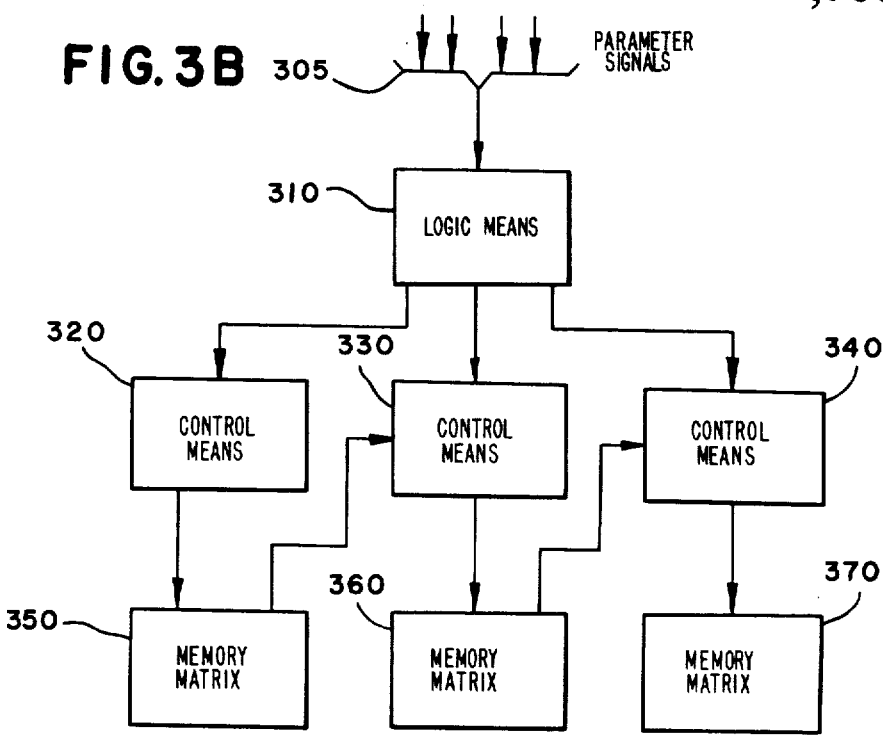
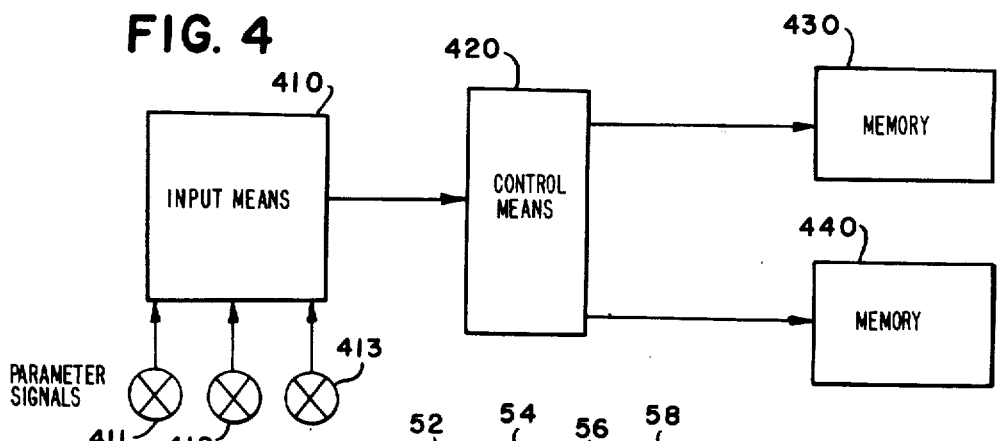
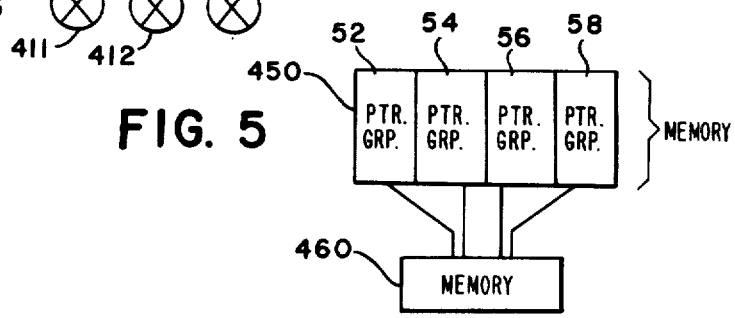

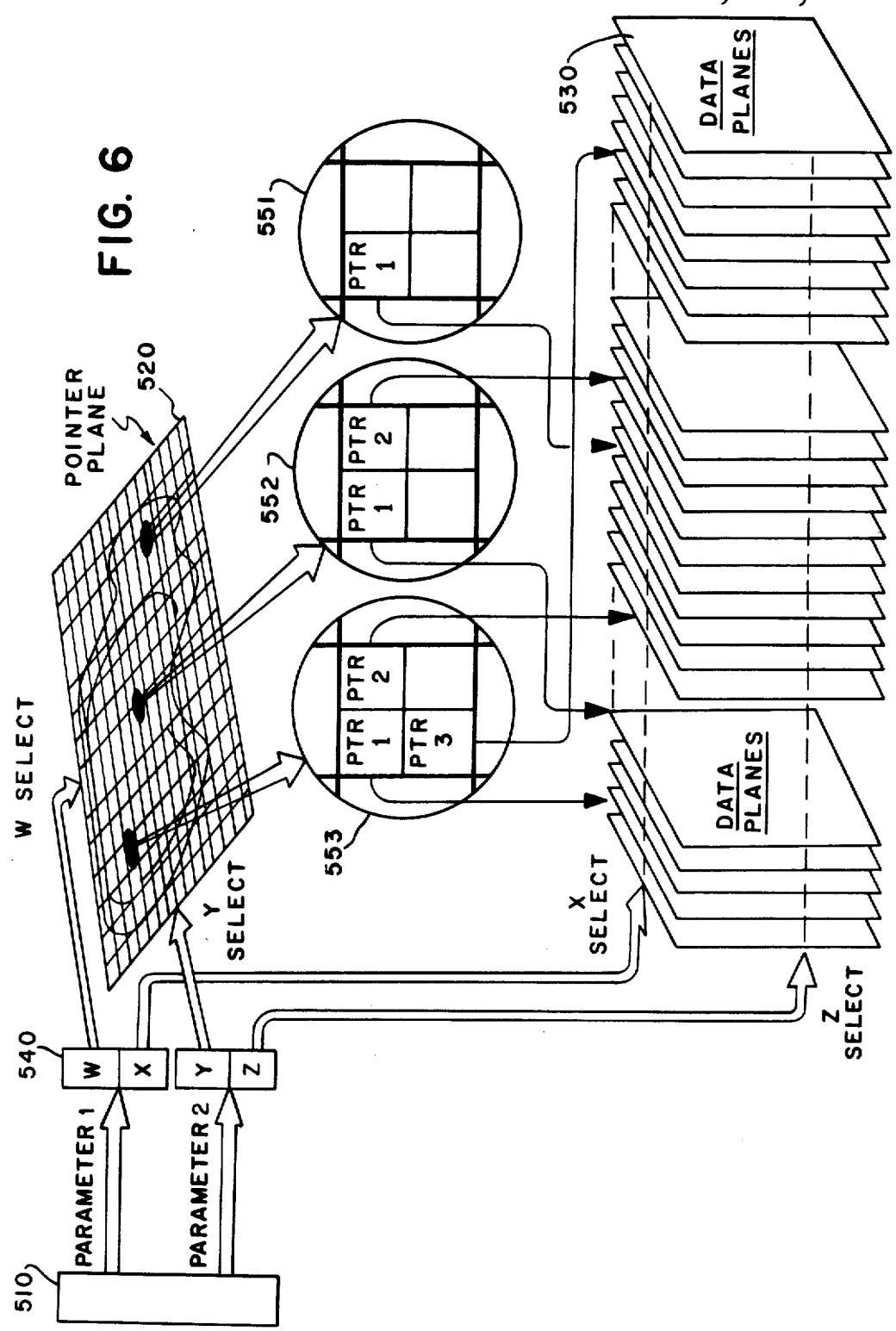

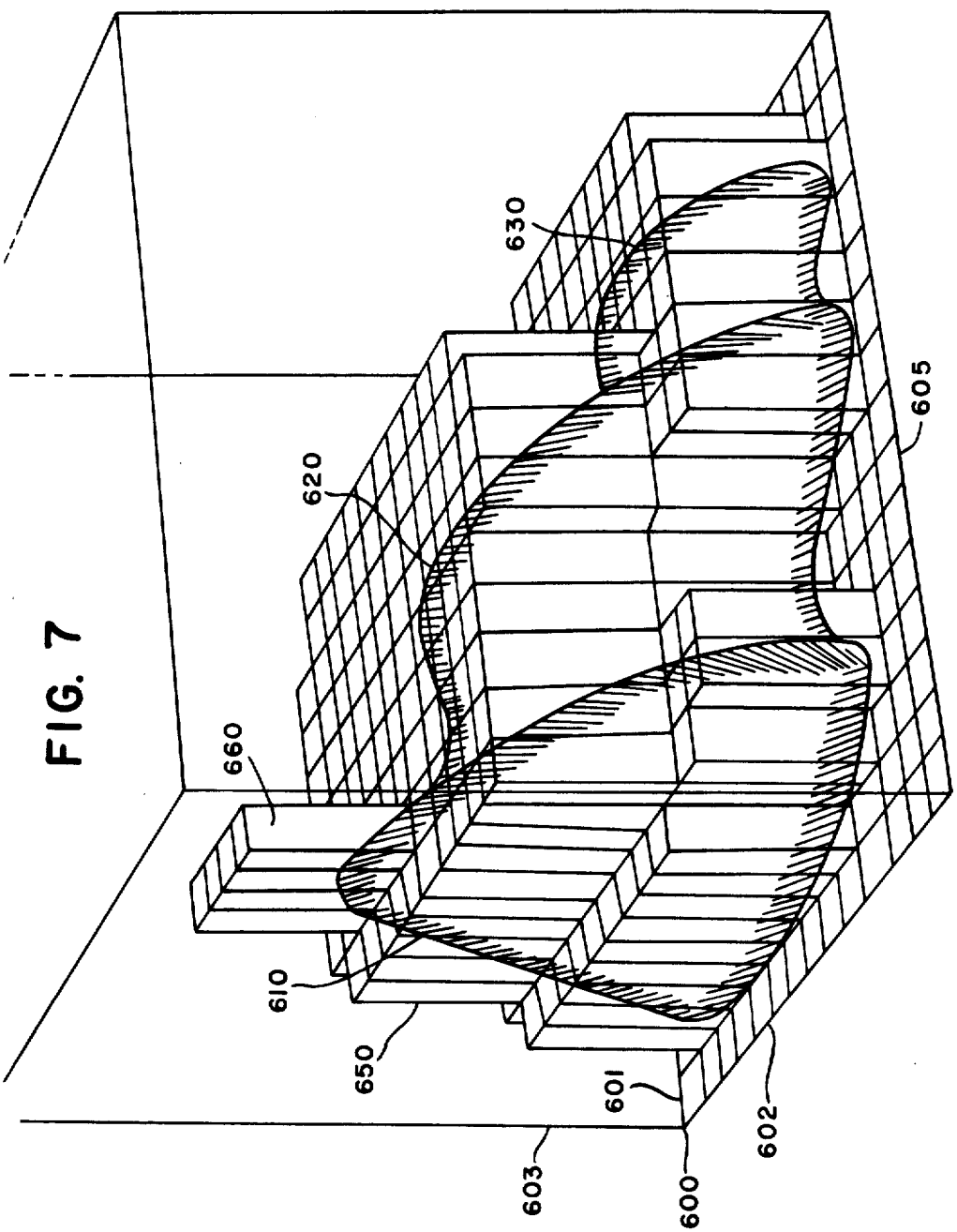

NOTES: XFS = MAXIMUM X-COUNT
ZFS = " Z COUNT

X = ADDRESS LO BYTE
Z = ADDRESS HI BYTE
Y = DATA (COUNT)

B = 0 DOUBLE PRECISION
B = 1 READY FOR BYTE #1
B = 2 READY FOR BYTE #2

DATA STORAGE SYSTEM HAVING MEANS FOR COMPRESSING INPUT DATA FROM SETS OF CORRELATED PARAMETERS

CROSS-REFERENCE TO RELATED APPLICATIONS

The present application is a continuation-in-part of application Ser. No. 434,623 filed Oct. 15, 1982 in the name of John L. Haynes, now abandoned.

BACKGROUND OF THE INVENTION

This invention relates generally to a data storage system and more specifically to a data storage system for reducing the amount of memory storage required to store sets of correlated data.

Data logging and analysis systems and data storage and compression systems, find applications in many diverse fields such as the medical area including cellular tissue analysis (cytology), X-ray analysis, and Cat Scan. These systems also find use in the fields of oceanography, seismography, meteorology and satellite weather photo based forecasting, and various other systems. A major problem in these systems is the memory storage size requirement which occurs when multiple parameters, each having multiple resolution levels, are to be cross-correlated into sets and the accumulated occurrences of each set counted.

For example, the cross-correlation of two parameters, each having 256 possible levels of resolution, requires 65,536 count storage locations. Similarly, cross-correlating four such parameters requires over four billion memory count storage locations, and cross-correlating five such parameters requires over one trillion count storage locations. In general, the number of count locations for these systems is $R^P$ where R is the number of resolution levels for each parameter and P is the number of parameters to be correlated. This number must then be multiplied by the number of bits needed to store the maximum count for any such correlated set to yield the total size of the memory. These enormous memory requirements are well beyond the primary and secondary storage capability of many present day computer systems except for a few extremely expensive supercomputers which are not practical for general use.

Additionally, real time data logging and correlation mandates the useof fast primary storage means, so as to avoid loss of incoming data. One approach has been to deal with the parameter data in a linear form, not cross-correlated, where each occurrence of each parameter signal for each level of resolution is logged and counter. Thus, where each parameter signal has one of 256 resolution levels, a system correlating two parameters would require 512 storage locations having a word length sufficient to store the maximum count which could be expected for any parameter at any signal resolution level. However, to derive meaningful information from the stored data in linear form, the parameter data must be cross-correlated, albeit not in real time, which still requires large amounts of memory storage.

SUMMARY OF THE INVENTION

In accordance with the present invention, a data storage system is provided with dynamically allocates storage space as needed. In one embodiment, the data storage system is comprised of means for receiving a plurality of individual parameter signals, first memory means for selectively storing pointer signals in a plurality of locations therein, second memory means for selectively storing occurrence count signals in a plurality of locations therein, and control means for associating occurrences of the parameter signals to the pointer signals in the first memory and for accumulating the occurrence count signals in the second memory responsive to respective occurrences of parameter signals at locations defined by the pointers.

The parameter signals which can be provided from any of numerous input sources, in general, have a plurality of values each corresponding to one of a plurality of degrees of resolution of a measured parameter. The first memory means provides for the storing of pointer signals in one of a plurality of locations responsive to the control means. The second memory provides means for selectively storing signals in one of a plurality of locations therein corresponding to the occurrence of an associated degree of resolution of a parameter signal and to an output data signal from the first memory. The control means provides means for selectively generating and storing the address pointer signals in one of a plurality of locations in said first memory reponsive to the parameter signal, such that an address pointer signal associatively links a selected one of the plurality of count locations in the second memory to a particular one of the degrees of resolution of a respective parameter signal. Additionally, the control means includes means for incrementing the count values stored in the associatively linked locations of the second memory responsive to an address pointer signal and the parameter signal, such that occurrences of particular combinations of parameter resolution levels are counted, and the count values stored. Alternatively, the means for incrementing the count values can be separate from the control means. In one embodiment of the present invention, the second memory locations can be provided such that count signals are stored in incremental values, such that a plurality of second memory locations can contain the count for the occurrence of a particular parameter combination.

In a preferred embodiment the data storage system provides for the compressed storage of the occurrences of cross-correlated sets of the various resolution levels of the parameter signals. Where the count storage in the second memory is incrementally stored, means can be provided in the first memory for storing incremental pointers to associated incremental counter locations for respective particular parameter signal occurrences.

In an alternate system embodiment, an encoding system is utilized to embed address jump and occurrence count data in a single memory. In this embodiment, a single memory is utilized for storage of parameter occurrence count and address position relative to a cross-correlated parameter input matrix so as to uniquely associate the occurrence count data to its respective set of cross-correlated parameters. The single memory provides recurring data signal partitions at fixed or variable word lengths, each partition containing a predefined number of subwords. The first subword defines the representative meaning of itself and the meaning of the following subword or subwords. Thus, the first subword of a partition can define whether it represents a count value for an associated parameter set, either alone or in combination with the other subword or subwords of the partition, or in combination with other partitions. Alternatively, the first subword of a partition can itself define a count value of a respective single cross-correlated parameter set and the other subword or subwords within the partition can each exclusively define the respective count for additional exclusive cross-correlated parameter sets. Alternatively, the first subword of a partition can define a logical address offset, relative to the input matrix, either alone or in conjunction with other subwords of the same partition, or of additional partitions. Further, the count value associated with the address offset value can be represented either within other subword words of the partition defining the address offset, within subwords of a contiguous partition, or can be defined in accordance with the previously discussed manner of count value representation as discussed above.

Other objects and advantages of the present invention will become apparent upon reading the following detailed description, while referring to the attached drawings, in which:

FIGS. 3A and 3B are block diagrams of a two and three memory level data storage system, respectively;

FIG. 4 illustrates another alternate embodiment of the system of FIG. 1;

FIG. 5 is a block diagram illustrating a partitioned count and pointer embodiment of the data storage system of FIG. 4;

FIG. 6 illustrates, both graphically and in block diagram form, a specific dynamic allocation and data compaction system and method, such as shown in FIGS. 1-5;

FIG. 7 illustrates a pictorial representation of a dynamic memory allocation as performed by the embodiment illustrated in FIG. 6;

Figure 13A:
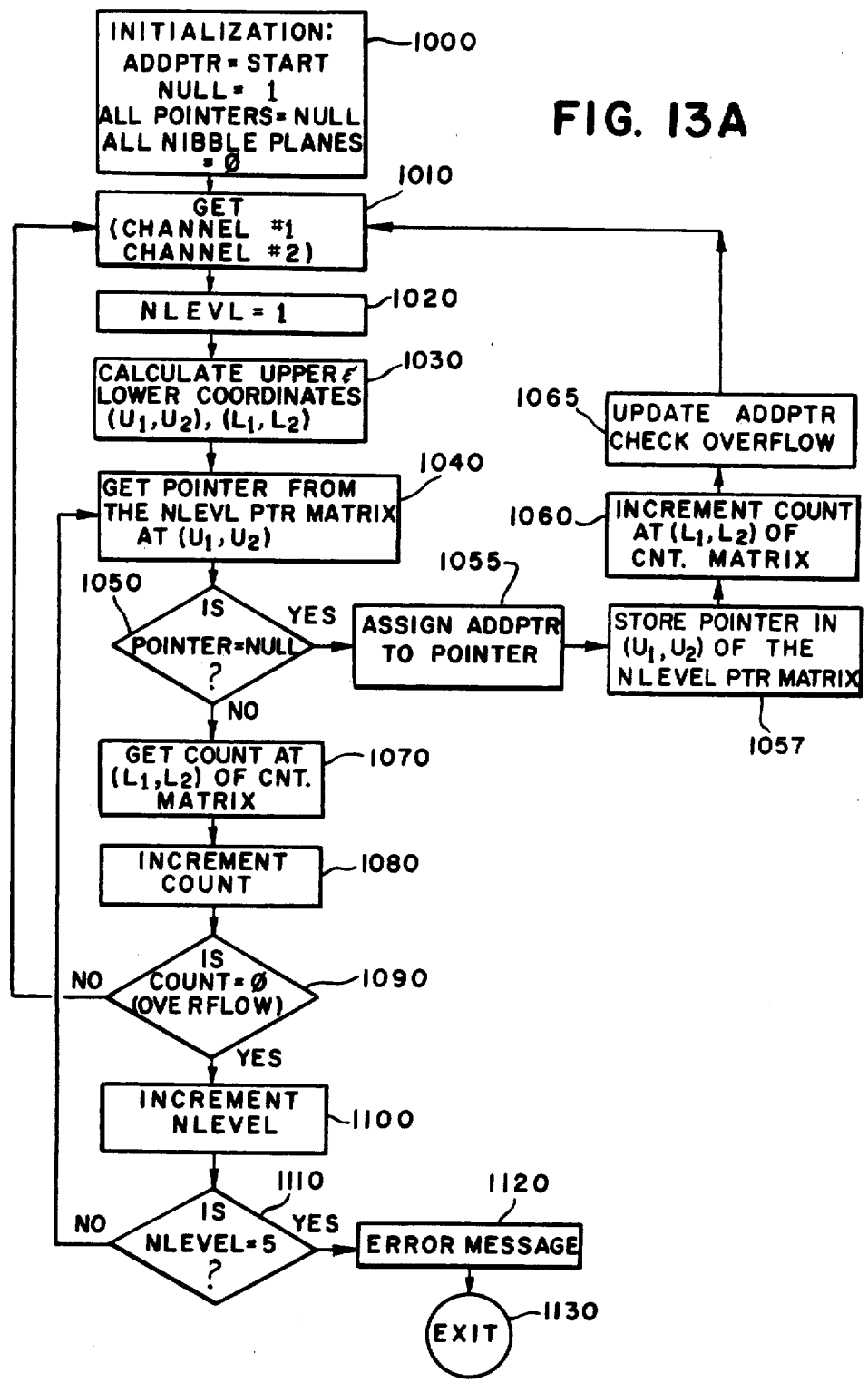
Figure 13:
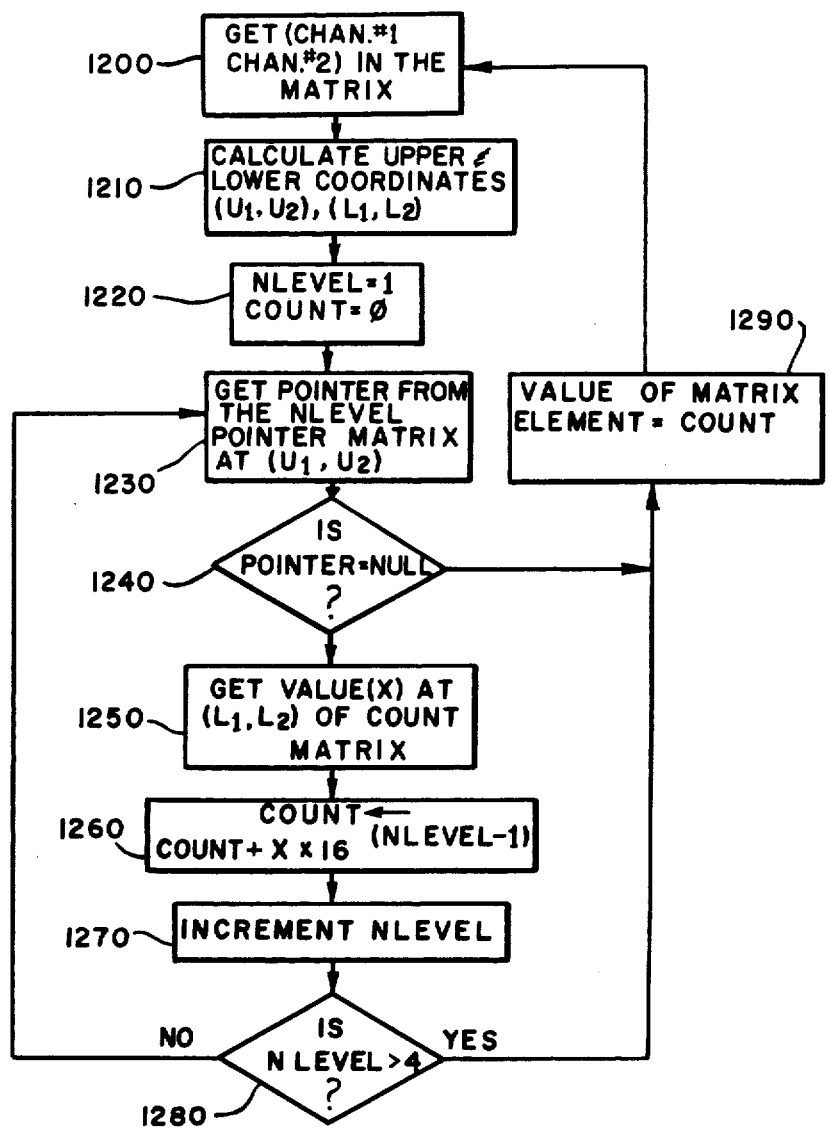
Figure 14A:
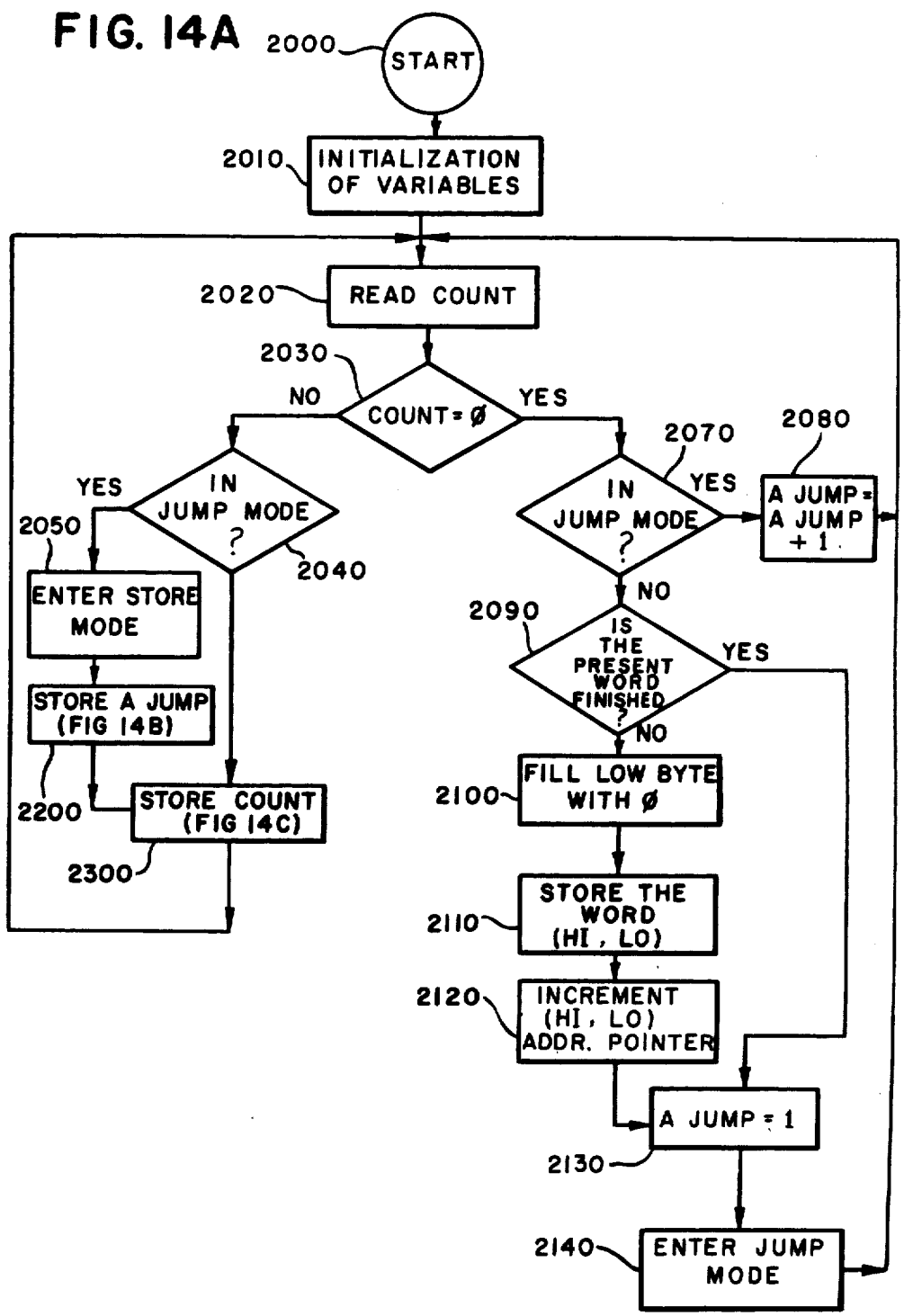
Figure 14B:
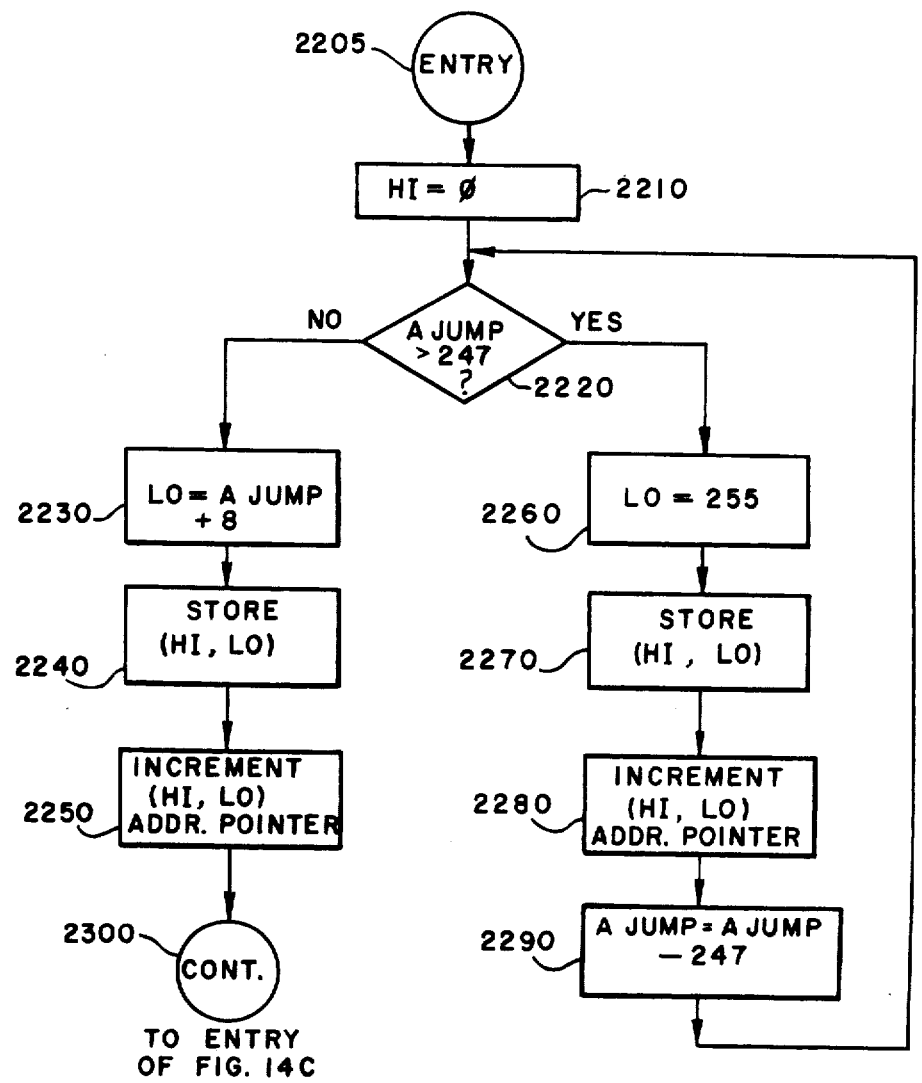
Figure 14C:
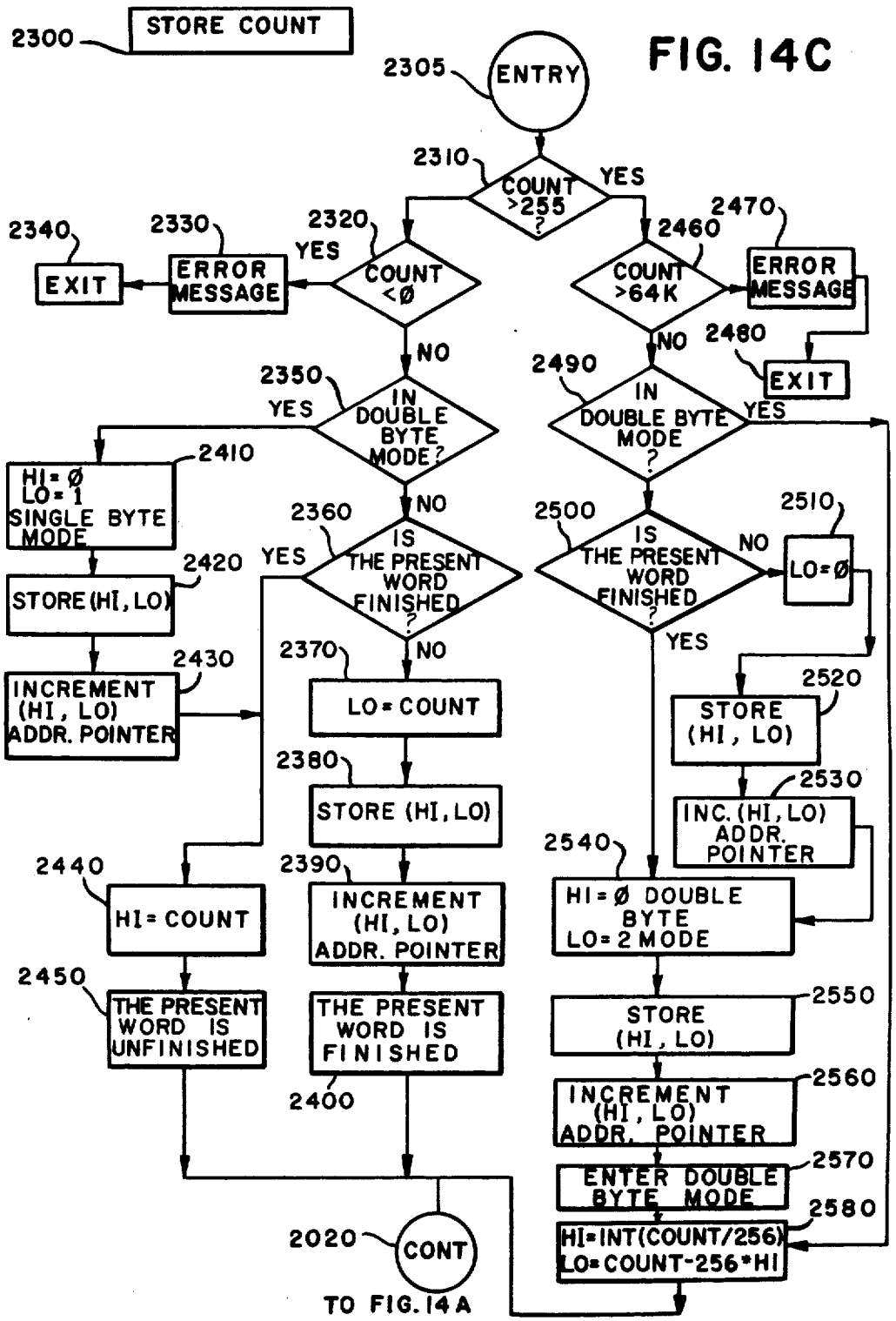
Figure 14D:
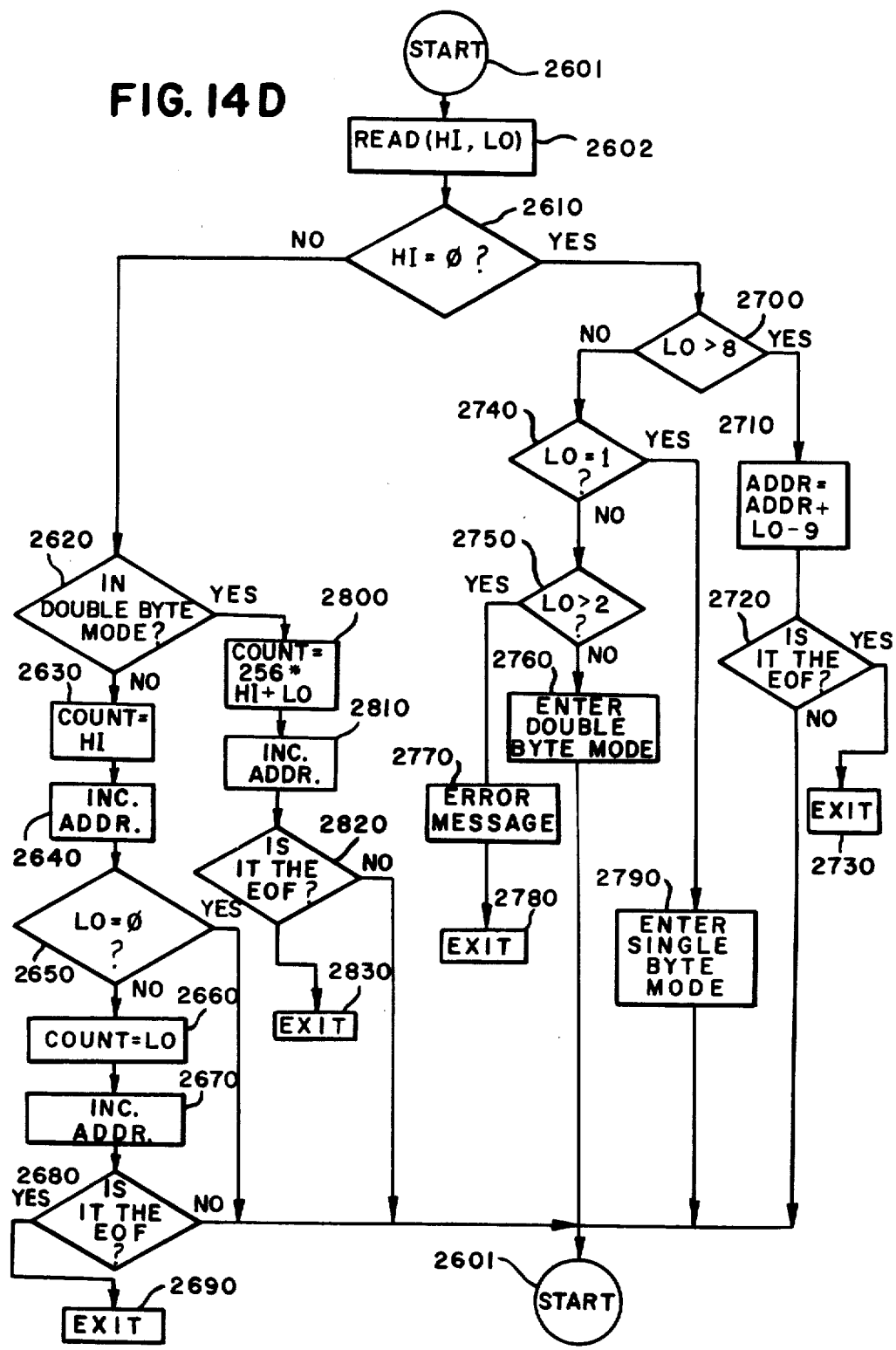
Figure 15A:
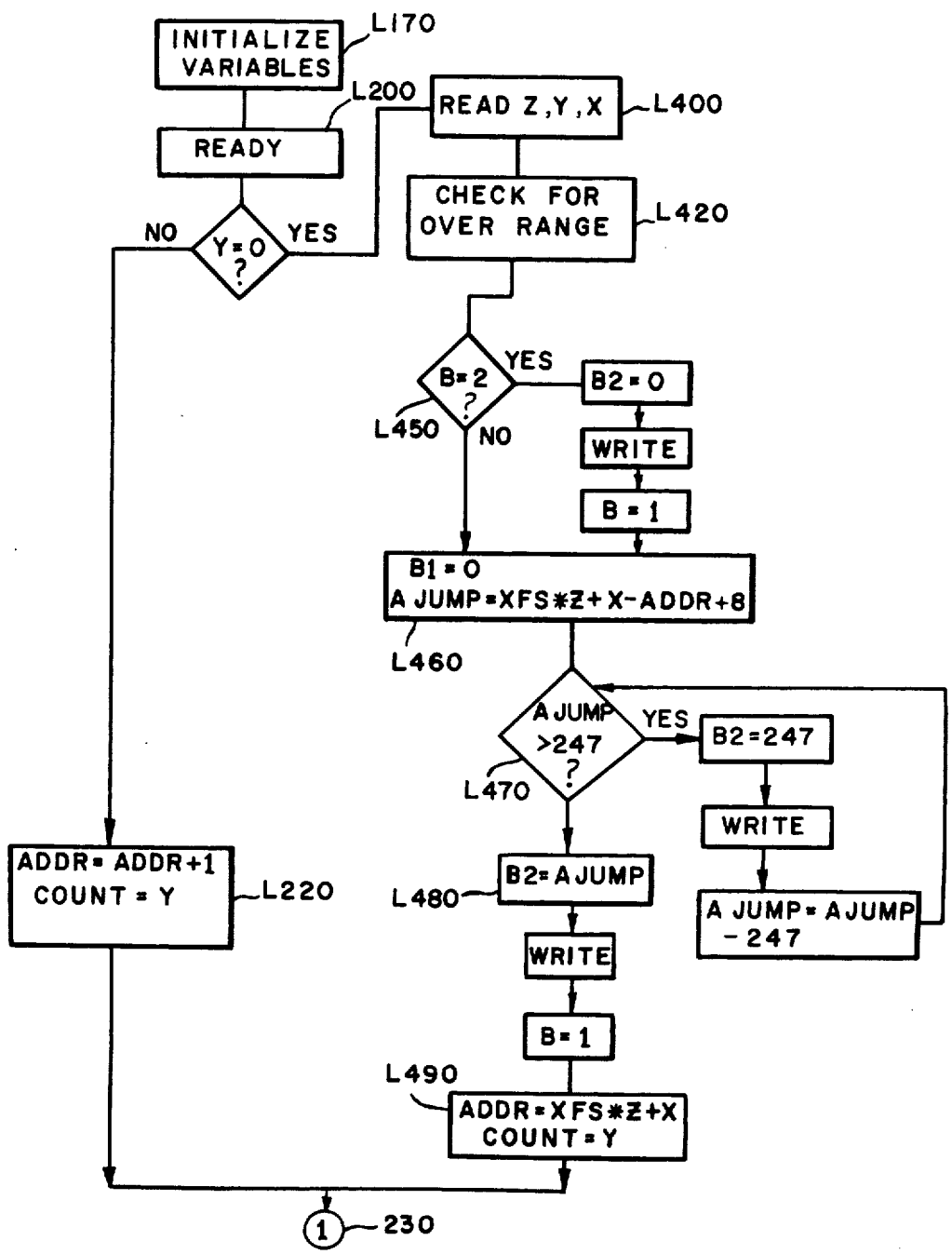
Figure 15B:
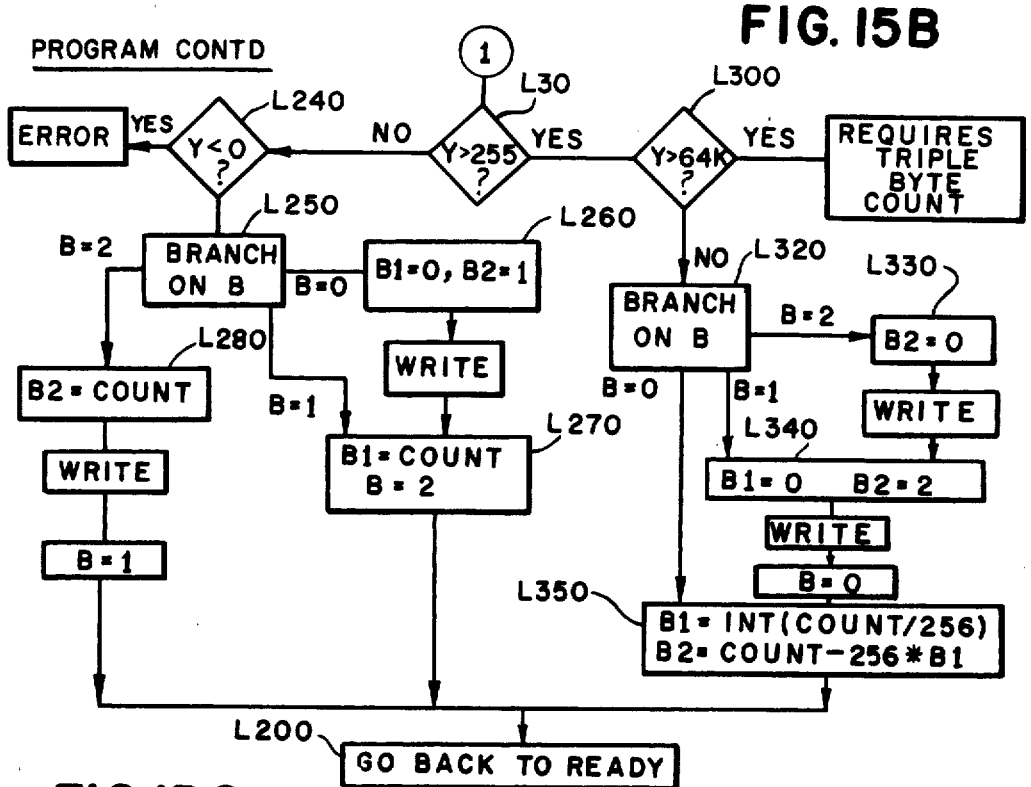
Figure 15C:
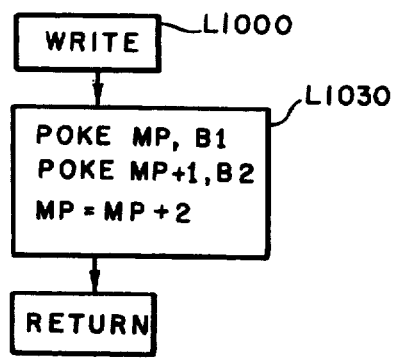
Figure 15D:
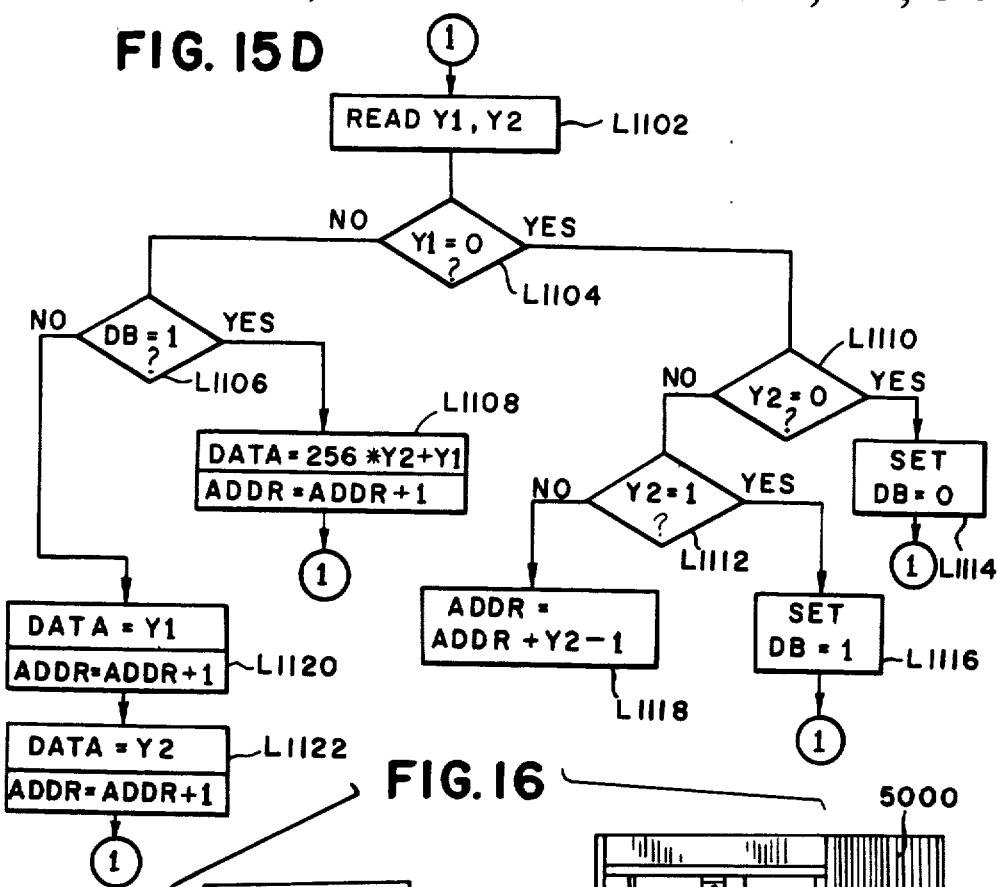
Figure 16:
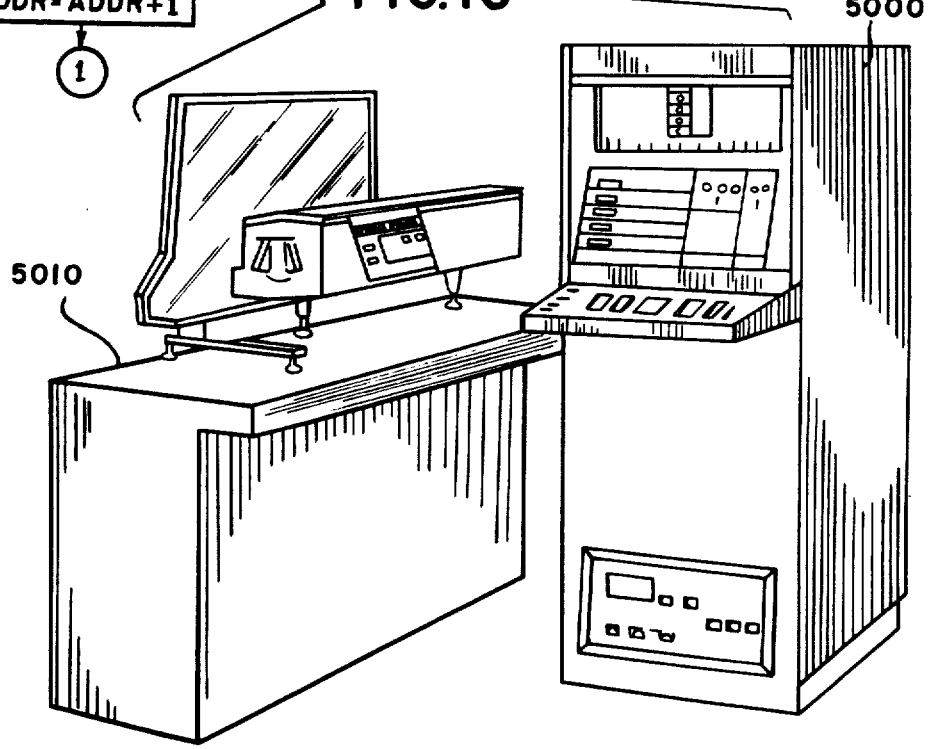
Figure 17:
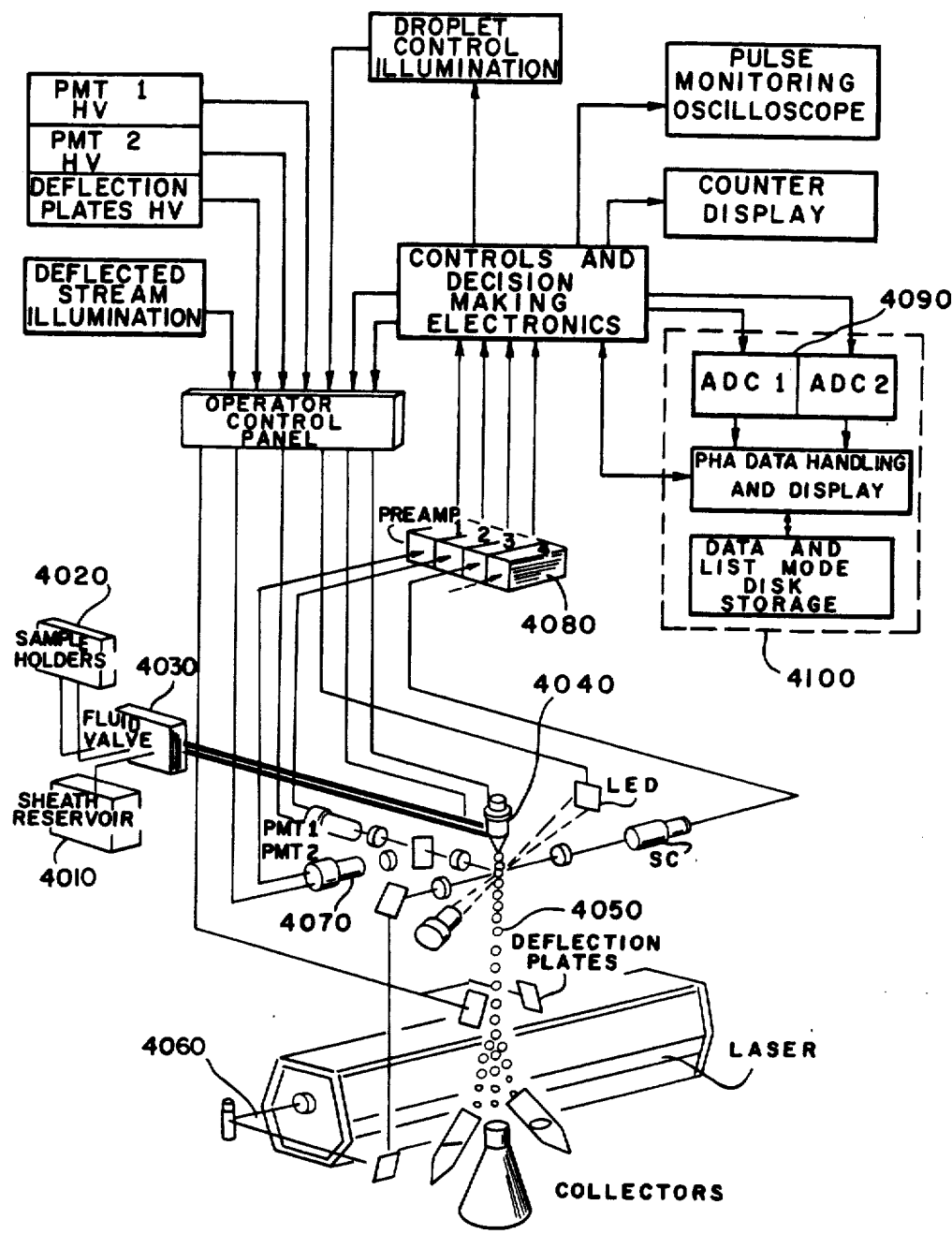

FIGS. 9-12 are illustrations of the count plane active memory requirements for parameter signal storage in accordance with the diagram of the alternate system, additionally illustrating the overhead and unutilized memory locations required by conventional systems, in addition to the active memory locations required by the alternate system, the FIGS. 9-12 respectively show byte resolution, nibble resolution, two bit per word resolution, and one bit per word resolution examples based upon empirically gathered data;

FIGS. 13-15 illustrate various logical flow charts which can be used to practice the data storage and compaction method of the present invention in combination with a programmable digital computer, wherein:

FIG. 13A illustrates a flow chart for a matrix-mapped data compaction;

FIG. 13B illustrates a flow chart for matrix-mapped data decompaction in accordance with one aspect of the present invention, as shown in the systems of FIGS. 1-6;

FIGS. 14A-C are flow charts for an alternate data compaction system and method in accordance with an alternate aspect of the present invention;

FIG. 14D is a flow chart for a data decompacton system and method for use in conjunction with the system and method of FIGS. 14A-C;

FIGS. 15A-C are flow charts of a specific computer program implementation of the compaction flow charts of FIGS. 14A-C;

FIG. 15D is a flow chart of a specific embodiment of the decompaction flow chart of FIG. 14D, for use in conjunction with the flow charts of FIGS. 15A-C;

FIG. 16 is a pictorial view of a FACS IV systems physical apparatus;

FIG. 17 is a block diagram of a FACS IV cell sorter system; and

Figure 18A:
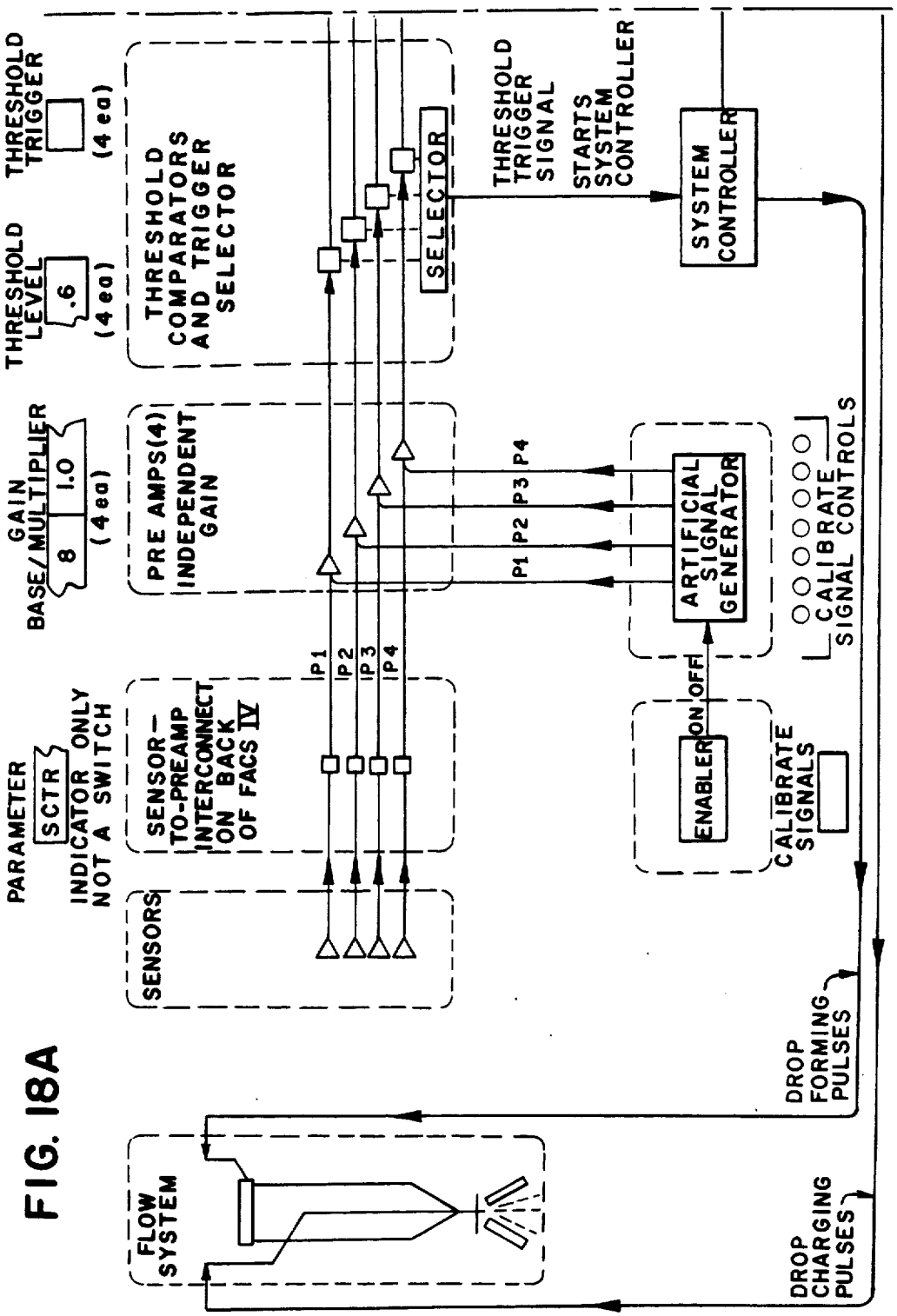
Figure 18B:
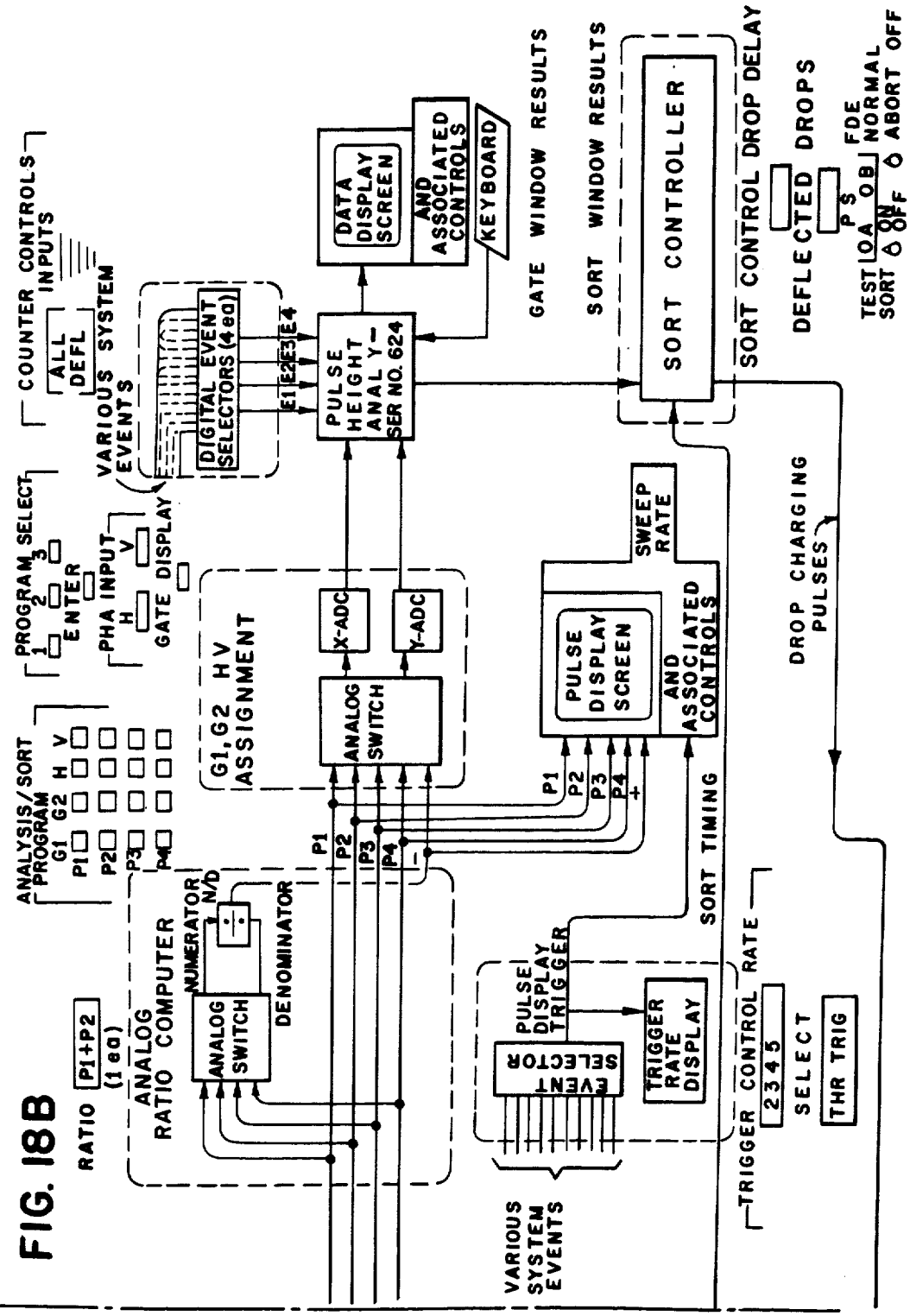

FIGS. 18A and 18B are an electronic functional block diagram of the FACS IV system of FIG. 17.

DETAILED DESCRIPTION OF THE PREFERRED EMBODIMENTS

Figure 1:
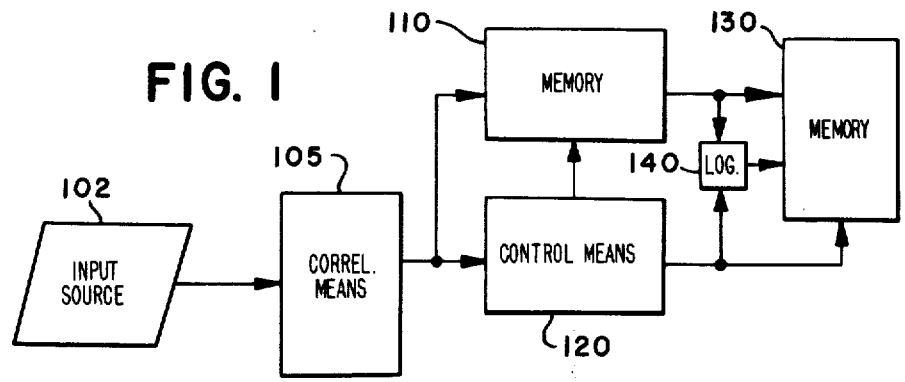
FIG. 1 is a block diagram of a first embodiment of a data storage system constructed in accordance with the invention

Referring now to FIG. 1, a data storage system in accordance with one embodiment of the present invention is shown. An input source 102 provides a plurality of individual parameter signals for utilization by the data storage system. The input can be from any of various sources, including previously stored and recalled data signals from memory or disk, or real time data logging inputs from a plurality of transducer sensors having their outputs signal processed and buffered to provide the plurality of individual parameter signals to the remainder of the data storage system. The input parameter signals are coupled to and passed through a data logging and correlation means 105 which selectively provide an active or presently occurring set signal from a plurality of set signals, each of the set signals corresponding to each potential cross-correlated combination of parameter signal values. The set signals output from the correlation means 105 are coupled to a first memory 110 and a control means 120.

The first memory 110 has a plurality of storage locations addressable responsive to said set signals. The control means stores selected first pointer signals in locations in the first memory responsive to active occurrences of the set signals. More specifically, the control means stores selected ones of a predefined plurality of first pointer signals where each first pointer signal is respectively associated with an active set signal. The control means stores the selected pointer signal in a selected first memory location responsive to the initial occurrence of the associated active set signal. The first pointer signal associatively links each actively occurring combination of parameter values to a counter storage location in a second memory 130. The second memory 130 has a plurality of storage locations addressable responsive to the first pointer signal and the respective associated active set signal. The accumulated count for the number of occurrences for each active set signal is stored in a corresponding location in the second memory. Logic means 140 accumulates and stores the count for the number of occurrences of each active set signal in a respective location in the second memory 130 responsive to the first pointer signal and the respective active set signal. Thus, memory storage locations in the second memory 130 are dynamically allocated as required, i.e., only for actively occurring combinations of parameter values. This is achieved without loss of the logical association of the stored count to the logical organization of the combinations of cross-correlated individual parameter signals.

In another embodiment there may also be provided additional address grouping means, which may be included in the input means 102 or the correlation means 105, for grouping sets of locations of first memory 110 into singularly addressable subgroup locations, such that each first pointer signal is responsive to and associated with a group address. In this embodiment, the control means 120 is further characterized in that each one of the first pointer signals corresponds to all of the set signals within a common group. Additionally, in this embodiment, this system is further characterized in that the particular location in the second memory for storage of the accumulated count is selected responsive to the first pointer signal and its associated group address. This embodiment of the invention can be seen more clearly in FIG. 6, and will be described later in greater detail with reference to that figure.

Figure 2:
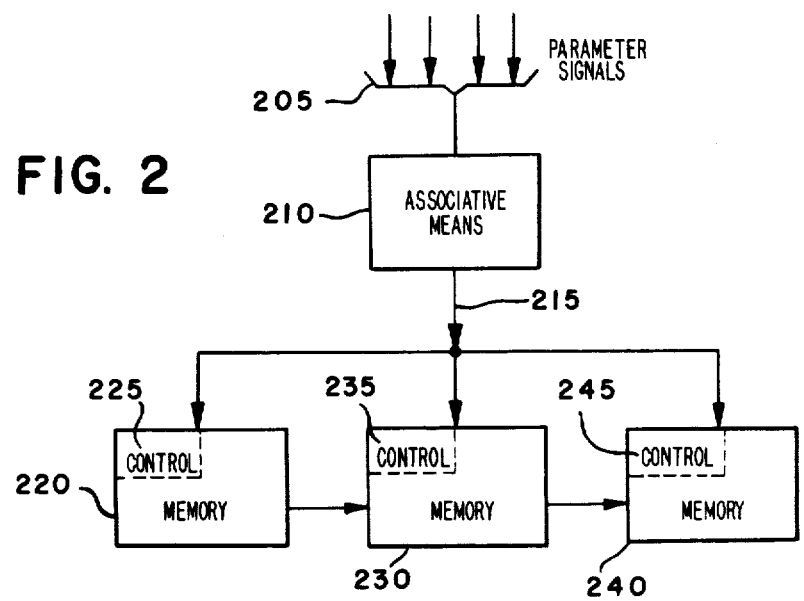
FIG. 2 illustrates an alternate embodiment of a system such as that of FIG. 1.

Referring now to FIG. 2, an alternate embodiment of a data logging and storage system of the present invention is shown. An input source (not shown in FIG. 2, but of the type as described with reference to input means of 102 of FIG. 1) provides a plurality of parameter signals 205, where each parameter signal has a plurality of resolution levels or values. The parameter signals 205 are coupled to an associative means 210. The associative means 210 provides a data correspondence address output via line 215 for each of the possible combinations of resolution values for the parameter signals such that each combination set has a unique data correspondence address associated therewith. The data correspondence addresses on line 215 are coupled to a first addressable memory 220, a second addressable memory 230, and a third addressable memory 240.

The first addressable memory 220 provides for the storage of a first pointer signal at a selected location within, the selected location being addressable responsive to the data correspondence address of a presently occurring combination. The second addressable memory 230 is comprised of a plurality of individual storage arrays, each individual storage array comprising a plurality of individual storage locations. The second memory array providing means for storing a second pointer within a selected location of a selected storage array of the second memory responsive to the associated data correspondence address 215 and the associated first pointer. The third memory 240 is comprised of a plurality of storage arrays, where each is addressable responsive to the second pointer as output from the second memory 230. Each storage array of the third memory 240 has a plurality of storage locations addressable by the data correspondence address associated with the first pointer means 245 and provides means for storing an accumulated occurrence count for the combination of resolution levels associated with each actively occuring data correspondence address.

In the embodiment of FIG. 2, a first control means 225 provides for selecting and storing a unique first pointer in the first memory, responsive to the initial occurrence of an associated set. The first control means, thus, dynamically allocates storage space within the second memory based upon actively occurring parameter signal combinations. Additionally, in this embodiment, a second control means 235 is provided for selecting and storing a unique second pointer in the second memory 230 responsive to the initial occurrence of a respective associated set of parameter signals and the associated first pointer signal. The location in the second memory for storage of the second pointer is defined responsive to the data correspondence address and the first pointer associated with the presently occurring set of parameter signals. In an alternate embodiment of the system of FIG. 2, the second memory array 230 and second control means 235 can be eliminated, with the first pointer signal addressing a location in the third memory 240 directly in combination with the data correspondence address. Thus, either double or single associative linking can be provided for.

Figure 3A:
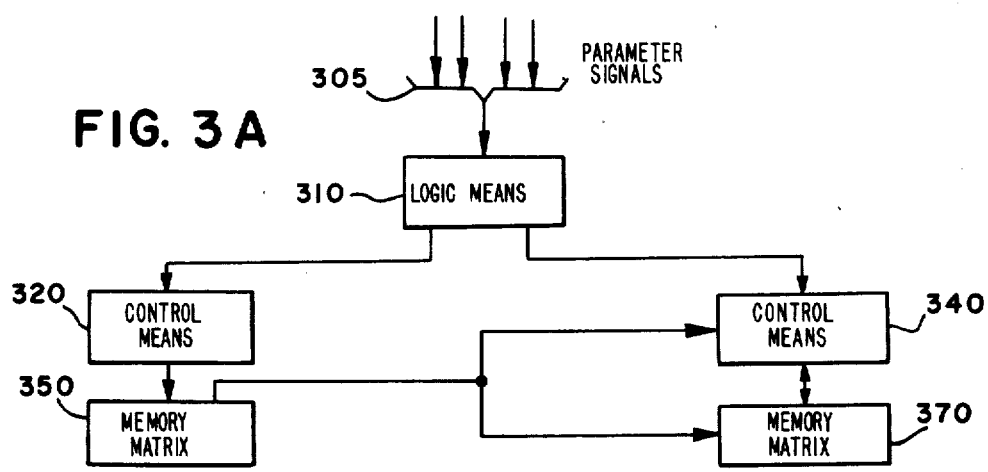

Referring to FIG. 3A, another embodiment of the system of FIG. 2 is shown. An input means, such as input means 102 of FIG. 1, provides a plurality of parameter signals 305 each having a plurality of resolution levels. A first memory matrix 350 and a second memory matrix 370 each have a plurality of storage locations. The input parameter signals are coupled to logic means 310 for associating first memory address locations with corresponding combinations of parameter signals such that each such combination is associated with a single addressable location within the first memory. As described later herein, with reference to FIG. 6, each such addressable location can be associated with a plurality of such combinations, although each such combination is only associated with a single addressable location within the first memory. The logic means 310 provides an output responsive to each occurrence of each combination, the output providing means for addressing a corresponding location in the first memory 350. The output from the logic means 310 is coupled to a first control means 320 and a second control means 340. The first control means 320 provides a first pointer signal addressing an unused second memory address location, the first pointer signal being stored in a selected first memory location responsive to the initial occurrence of a corresponding combination of parameter signals as generated by the output of the logic means 310. The first control means 320 can address the first memory 350 for storage or for the output of first pointer data. The second memory, 370, is comprised of a plurality of counter matrices, each memory counter matrix comprising a plurality of counter locations, and each of the counter matrices being addressable responsive to a first pointer, as output from the first memory 350. Individual locations within the counter matrix being addressable responsive to the output from the logic control means 310, either directly, or a coupled thereto via the second control means 340. The second control means 340 provide means for acumulating and storing count data representative of the frequency of occurrence of a combination of parameter signals. The second control means operates in response to the second pointer and the output from the logic means 310 (indicative of the occurrence of the combination).

In another embodiment of the system in FIG. 3A, the first memory 350 is first characterized as comprising a plurality of partitioned groups of pointer locations, and the second memory 370 is further comprised of a plurality of partitioned groups of counter locations for storing combination occurrence counts on an incremental basis. Each of the groups of pointer locations in the first memory 350 is associated with an address of a respective group of counter locations in the second memory 370. Means are provided, either within the second control means 340, or separately, for storing a first incremental pointer in the first memory 350, at a location within a group, addressing the next higher level of the first memory which is associated with the overflowed counter location group of the second memory. The first incremental pointer addresses a counter location in the second memory of the next incremental group relative to the group of the overflowed counter location in the second memory. Thus, without reserving groups of incremental locations in the second memory 370 for storage of incremental associated counts, the system dynamically allocates counter memory on an incremental basis. As shown and discussed with reference to FIG. 5, and later in greater detail with reference to FIG. 6, the first memory can permanently allocate multiple locations defined as incremental group levels for each addressable location, storing pointer signals within those locations as needed. This simplifies the associative linking apparatus and method of the present embodiment as compared with the alternative technique of dynamically linking multiple pointers within the first memory to a particular first memory location, such as via a linked list.

Referring now to FIG. 3B, an alternative embodiment of the system of FIG. 3A is shown. The figure illustrates a three memory embodiment of the system of FIG. 3A, which is identical to that system, except for the interposition of a third control means 330 and a third memory 360 between the first control means 320 and first memory 350, and the second control means 340 and second memory 370. The third memory 360 is comprised of a plurality of addressable submatrices. The storage locations within the third memory 360 are addressed responsive to the first pointer signal and the output of the logic means 310, either directly, or as coupled via the third control means 330. The third control means 330 provide a second pointer for storage in a selected matrix of the third memory 360 responsive to the initial occurrence of a corresponding combination of parameter signals. In this embodiment, the second pointer signal, as output from the third memory 360, is coupled to the second control means 340. The second control means 340, accumulates and stores the count data representative of the frequency of occurrence of a respective combination of parameter signals responsive to the second pointer, as output from the third memory 360, and the occurrence of said combination, as indicated by the output of logic means 310.

Referring now to FIG. 4, still another embodiment of a data storage system constructed in accordance with the present invention is shown. Input means 410 provide selected ones of respective parameter signals corresponding to each one of a plurality of degrees of resolution of a measured parameter signal. A single parameter input signal 411, or a plurality of input parameter signals 411, 412 and 413, are shown coupled to the input means 410. The parameter signal input 411 (and where applicable 412 and 413) can either represent processed transducer inputs or can represent data storage means which input previously stored processed parameter signals. The respective parameter signal outputs of the input means 410 are coupled to a control means 420. The control means 420 provide outputs for coupling to a first memory 430 and a second memory 440. The first memory 430, illustrated as a random access memory, provides means for selectively storing data signals in a plurality of locations. The second memory 440 provides means for selectively storing data signals in a plurality of locations therein, responsive to the occurrence of a parameter signal as output from the input means 410. The control means 420 selectively stores an address pointer signal, pointing to an unused location in the second memory 440, in one of the plurality of locations in the first memory means 430 responsive to the initial occurrence of an associated parameter signal. The address pointer signal stored in the first memory 430, associatively links a selected one of the plurality of locations in the second memory to a particular one of the combinations of parameter signals. The control means 420 can further include means for incrementing the signal values in selected ones of the associatively linked locations of the second memory in response to the address pointer signal and the parameter signal. Alternatively, the means for incrementing can represent a separate means for the control means 420. As described above, the input means can provide for either a single multivalue parameter signal, or can provide a plurality of individual parameter signals, with each individual parameter signal corresponding to a one of the plurality of degrees of resolution for a measured individual parameter, such as parameters 411, 412 and 413.

In the embodiment of FIG. 4 where a plurality of individual parameter signals are provided, the system can further be comprised of means for storing data signals since selected ones of the plurality of locations of the first memory are responsive to the occurrence of sets of individual parameter signals. This means can be part of the control means 420, or can be separately provided for. Thus, each cross-correlated set is associated with a particular addressable location within the first memory and with a particular first pointer signal therein for all active occurrences of correlated sets of individual parameter signals. In this embodiment, the stored count signals in the second memory are responsive to and representative of the number of occurrences of the possible degrees of resolution of either individual parameter signals, or of associated unique sets of said correlated individual parameter signals.

In an alternate embodiment of the system of FIG. 4, as shown in FIG. 5, each of the second memory locations is of a fixed word size having a predefined value of a maximum count storage which can be contained within each of the second memory locations. Referring to FIG. 5, the first memory is represented as 450, and the second memory is 460, corresponding to the first memory 430 and second memory 440 of FIG. 4. In this embodiment, the control means 420 provides means for indicating an overflow of the stored count value in a second memory location. The overflow is detected by sensing when the stored signal in a second memory location exceeds a predefined value. The control means 420 additionally provides means for selectively storing and associating a second pointer in a location in said first memory responsive to the overflow indication. The associative second pointer signal addresses a location in the second memory for storing data signals responsive to and representative of a number of occurrences greater than the predefined number of occurrences of the respective associated degrees of resolution of the individual parameter signals to which the respective overflow indication is responsive. As illustrated in FIG. 5, the first memory 450 is partitioned into four pointer groups 52, 54, 56, and 58 for each addressable location. Thus, for the system illustrated in FIG. 5, each correlated set of parameter signals can have associated therewith four incremental count storage locations in the second memory 460. However, additional or lesser numbers of groups of pointers associated with a particular addressable location in the first memory 450 can be provided for.

Referring to FIG. 6, a combination electrical block diagram and graphical illustration of a specific embodiment of a dynamically allocated memory and compaction system having incremental count storage is shown. As illustrated in FIG. 6, an input means 510 provides parameter signals parameter 1 and parameter 2. The input means 510 can be of the same type as described with reference to the FIG. 1 input means 102. Each of the parameter signals parameter 1 and parameter 2, has one of a plurality of n values corresponding to one of a plurality of n degrees of resolution. The input means 510 includes means for associating a unique address with each of the plurality of n values of each of the respective parameters. Associative means 540, containing separate associative means for each of the parameter signals, parameter 1 nad parameter 2, decode the associative address of the active parameter set from the input means 510, providing two subaddress select signals.

The first subaddress select signal, w select and y select, for each of the active parameter signals, parameter 1 and parameter 2, is used to address and select a particular location in the first memory 520. The first memory 520 forms a pointer plane containing pointers to a plurality of data planes of the second memory 530. The second part of the subaddresses for each of the parameters, parameter 1 and parameter 2, provides an address select signal, x select and z select, for addressing respective row and column locations in the data planes of the second memory 530. Thus, a stored pointer signal output from a selected first memory location addresses and selects a particular data plane from within the second memory 530. The combination of the pointer signal from the first memory and the x select and Z select signals from the associative means 540, act together to address a particular location within the second memory data planes for storage of a count value associated with the respective combination of parameter 1 and parameter 2 signals. The associative means 540 can further comprise control means for selectively storing address pointers to unused locations in the second memory 530 responsive to the initial occurrence of a particular correlated set of parameter 1 and parameter 2 signals. The pointer signals stored in the second memory 530 can be looked up from a table of unused second memory locations, can be computed from a base value plus an offset (e.g., add a fixed offset value to the last used pointer value), can be popped off a pointer stack or otherwise generated.

FIG. 6 illustrates the specific case of the second memory 530 having the capacity for four incremental counter locations per combinational set of parameter occurrences. The first memory 520 functions as a pointer plane, having a plurality of addressable locations responsive to the subaddress of the associative address of the correlated parameters, parameter 1 and parameter 2. Each addressable location in the first memory 520 has four storage locations allocated to it. Exploded views 551, 552, and 553, detail three of the adressable locations within the first memory 520. Exploded view 551 shows a first memory location containing a single pointer PRT1 addressing a single memory location within the second memory 520. Thus, only a single incremetal word is utilized for storing count values for the particular combination of parameter 1 and parameter 2 signals associated with the pointer value stored at location 551. Exploded view 552 shows a second addressable location within the first memory 520, having two pointer values associated with the single addressable location which in turn point to two individual memory locations in the second memory 530, thus, providing two incremental words for storage of the count associated with the combination of parameter 1 and parameter 2 signals associated with the first memory location 552.

As discussed above herein, the second pointer, PRT2 is provided and stored in the second allocated location of the commonly addressable group 532 responsive to the memory location in the second memory 530 associated with the first pointer PTR1 having overflowed. Upon an indication of an overflow the second pointer PTR2 is stored in the first memory 520 pointing to a previously unused location in the second memory. Thus, the pointers PTR1, PTR2 and the commonly addressable location 552 of the first memory 520 provide means for logically associating noncontiguous physical locations in the second memory 530 with a single combination of the parameter 1 and parameter 2 signals.

The exploded view 553 of a group of first memory locations of a commonly addressable cell illustrates a three word incremental count case of this incremental count system. In this case, both the first and second counter storage locations in the second memory 530 associated with the first and second pointers PTR1, PTR2 of the location 553 have overflowed, resulting in the provision of a third pointer PTR3 to a third location in the second memory 530. Thus, three physically noncontiguous locations in the second memory 530 are logically linked together to form an incremental count value associated with a single combination of the parameter 1 and parameter 2 signals.

As a specific example, parameter 1 and parameter 2 can each have an eight bit address associated with the plurality of values (256) of the respective signals. The four most significant bits of each of the associated parameter addresses correspond to the w select and y select signal which defines a particular location of a 16×16 addressable pointer memory matrix (first memory 520). Upon the initial occurrence of a particular w select and y select signal pair, a pointer value is provided for storage in the associated addressable location for pointing to a previously unused data plane in the second memory 530. Additionally, upon the initial occurrence and thereafter, the occurrence of a w select and a y select signal causes the pointer signal value to be output so as to address the second memory to choose the particular data plane within the second memory 530. Concurrently with the generation of the y select and w select signals, the associative means 540 provide the x select and z select signal corresponding to the least significant four bits of the parameter 1 and parameter 2 signals, respectively. The x select signal defines and addresses which row of the second memory 530 data plane is selected, while the z select signal defines and addresses a particular column location with the selected data plane. Thus, the location in the second memory 530, for storage of a count value indicative of the number of occurrences of an associated combination of the parameter 1 and parameter 2 signals, is selected and addressable responsive to a pointer signal from the first memory 520, and to the x select and z select signals from the associative control means 540. The eight bit associative addresses, and the four bit subaddresses were chosen for illustrative purposes only. Other associative address word lengths and subaddress word lengths, as well as nonsymmetric allocation word lengths for the first and second subaddress words can be implemented consistent with the present invention.

Since it has been found that the majority of memory utilization occurs at the second memory level, and that the data storage within the second memory is sparse, the dynamic allocation scheme of the present invention provides the benefits of reduced memory storage requirements while maintaining complete data storage capability and the associative linking of count values to parameter combinations. Also, since the first memory 520 only requires storage locations as defined by the subaddress select signals, the memory requirements of the first memory are very small compared to the storage requirements of the second memory 530 which requires at least one storage location for each actively occurring combination of the parameter 1 and parameter 2 signals.

Referring now to FIG. 7, an isometric view of a dynamically allocated memory system as shown in FIG. 6 is illustrated. The three darkened mounds 610, 620 and 630 illustrate the utilized data planes of the totality of available data planes represented by the cubic outline. The axis 601 is parameter 1, corresponding to W select. The origin 600 is in the far lower lefthand corner, such that a parameter 1 runs along the back lower edge. The axis 602 for parameter 2 is oriented into the paper corresponding to the Y select signal of the previous drawing. The vertical axis 603 corresponds to the accumulated value of the count. The count value shown in FIG. 7 is actually the $\log_2$ of the data count value stored in a cell. The pointer plane 520 is graphically equivalent to the bottom plane 605, of the isometric drawing of FIG. 7, with the selected cells corresponding to the downward intersection point of the data planes 650 to the bottom horizontal plane 605 of the isometric figure. In other words, the intersection of the utilized data planes 610, 620 and 630 with the bottom base plane 605 represents a footprint of the pointer plane's selected locations. The utilized data planes 610, 620 and 630 of FIG. 7 represent the active data memory locations of the data plane memory 530 of FIG. 6. The pointer plane first memory 520 of FIG. 6 acts as a contour map of the data plane storage allocation. The bottom of the isometric figure has a 1 to 1 correspondence with the pointer plane, but is not the same as the pointer plane. Each one of the 3-dimensional rectangular 660 squares in FIG. 7 which is above the bottom plane 605 is equivalent to a data plane of the secondary memory 530 FIG. 6.

The darkened area 610, 620, and 630 of FIG. 7, representing the data plane utilization required with the file compaction-dynamic allocation system of FIG. 6, can be seen to require less memory than would be the total number of data planes 650 required where parameter mapping was directly to the data planes, without utilization of the present invention, as shown by the total area of the data planes represented by the rectangular structures of FIG. 7.

Figure 8:
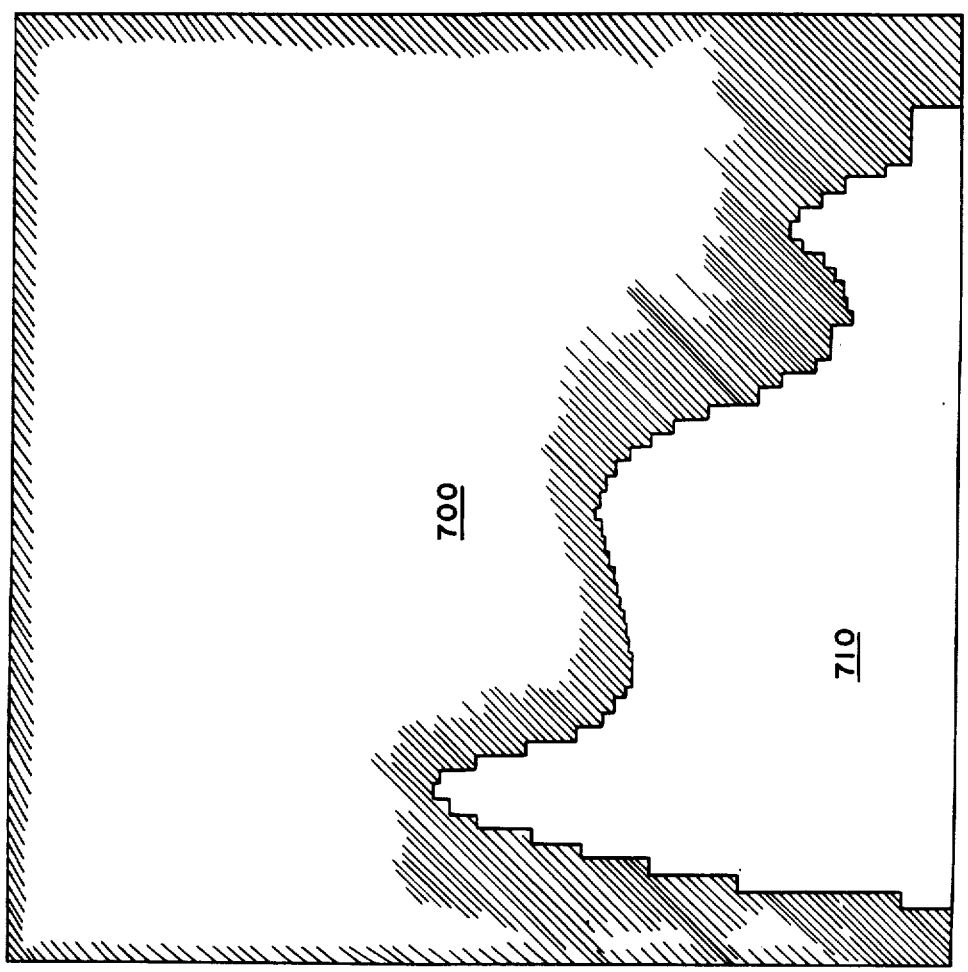
FIG. 8 represents a planar front view of the diagram of FIG. 7, illustrating the encoding of one parameter in accordance with the apparatus and method of the alternate data compaction system.

FIG. 8 represents a front view of the isometric figure of FIG. 7. This provides a single parameter footprint representative of the encoding technique of FIGS. 6 and 7. Particularly, the horizontal axis of FIG. 8 represents parameter 1 corresponding to FIGS. 6 and 7, and the vertical axis represents the $\log_2$ of the count value stored in the data locations. The combination of the darkened surface area 700 and the white surface area 710 represents, respectively, the unutilized memory words, and the utilized or active data parameter signal memory words, respectively, of a data plane memory utilizing conventional techniques. In the ideal data storage system, the required memory word utilization is reduced to that as outlined by the white area 710 of FIG. 8.

Figure 9:
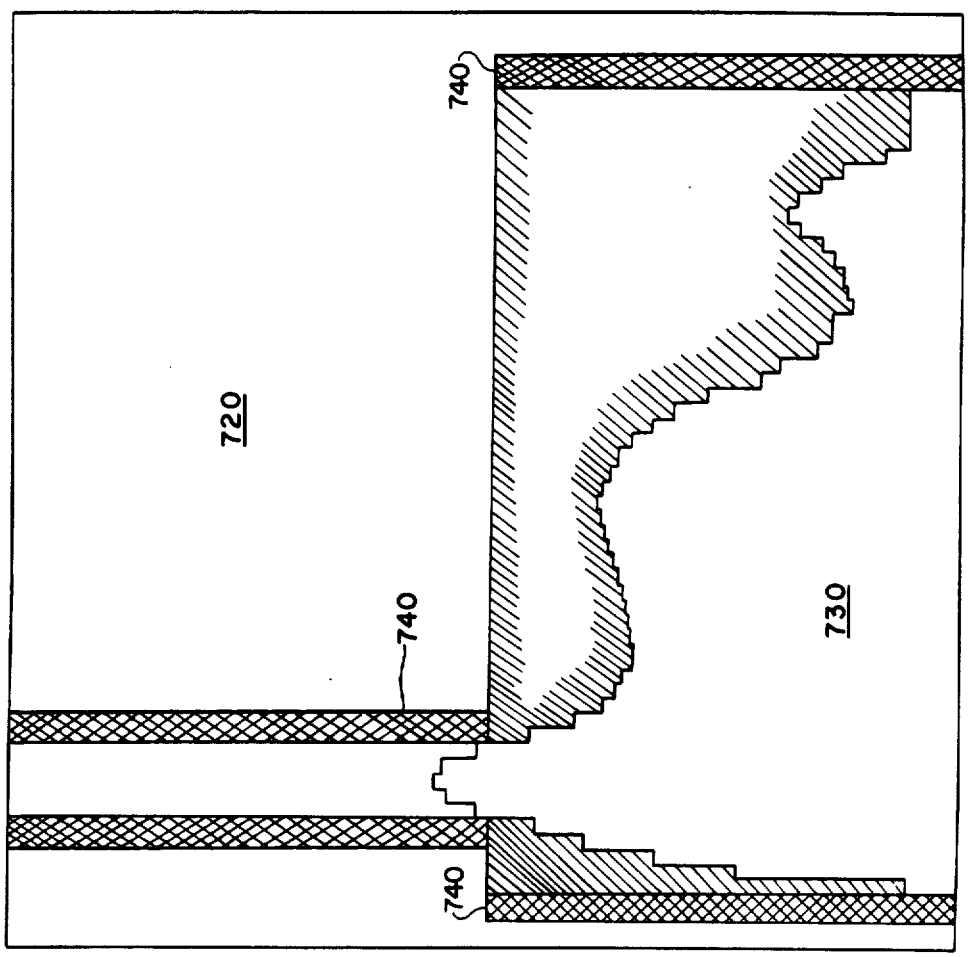
Figure 10:
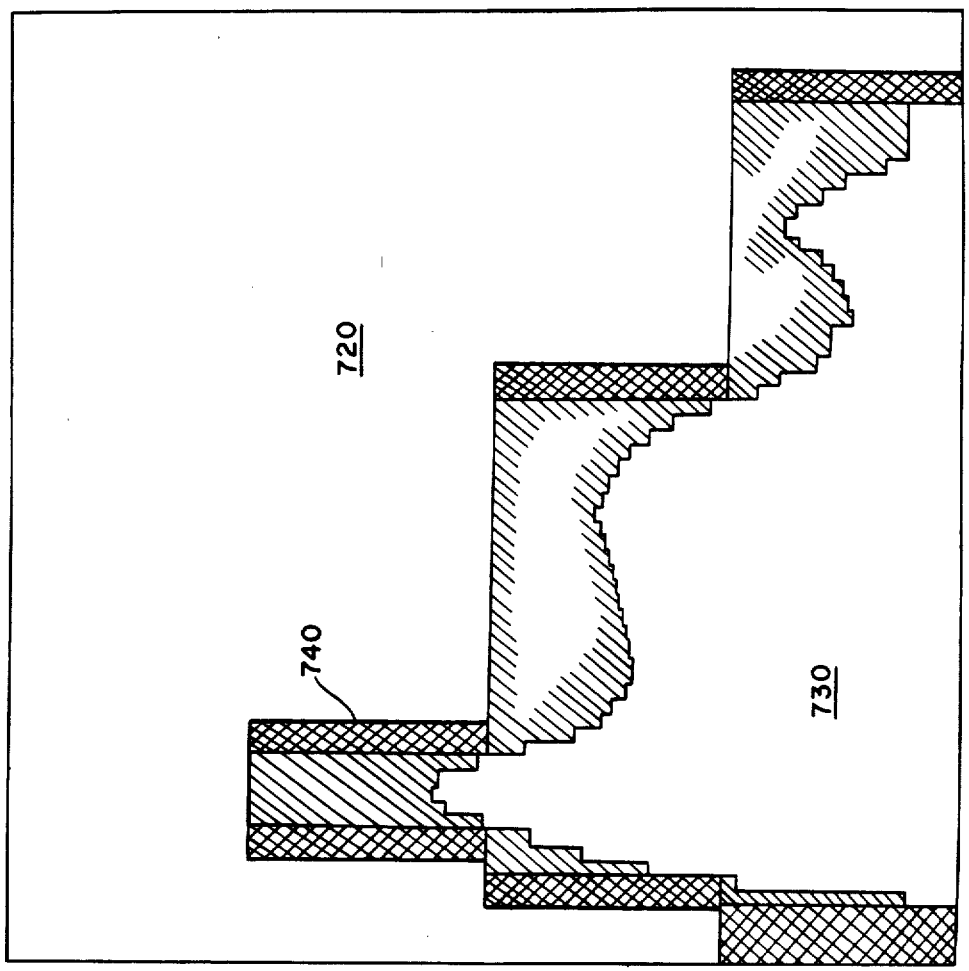
Figure 11:
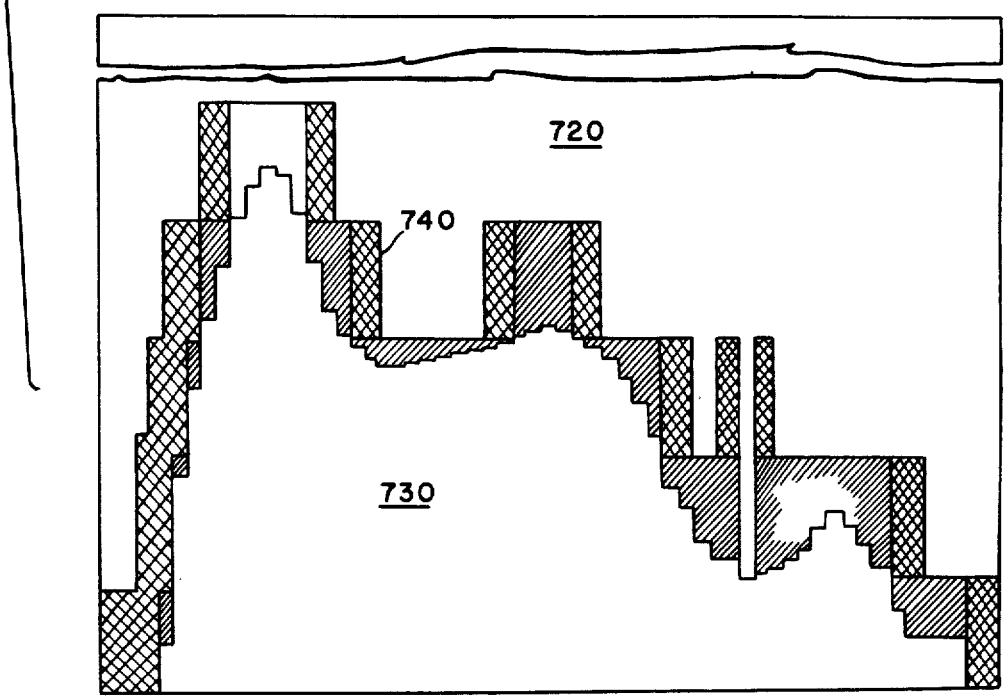
Figure 12:
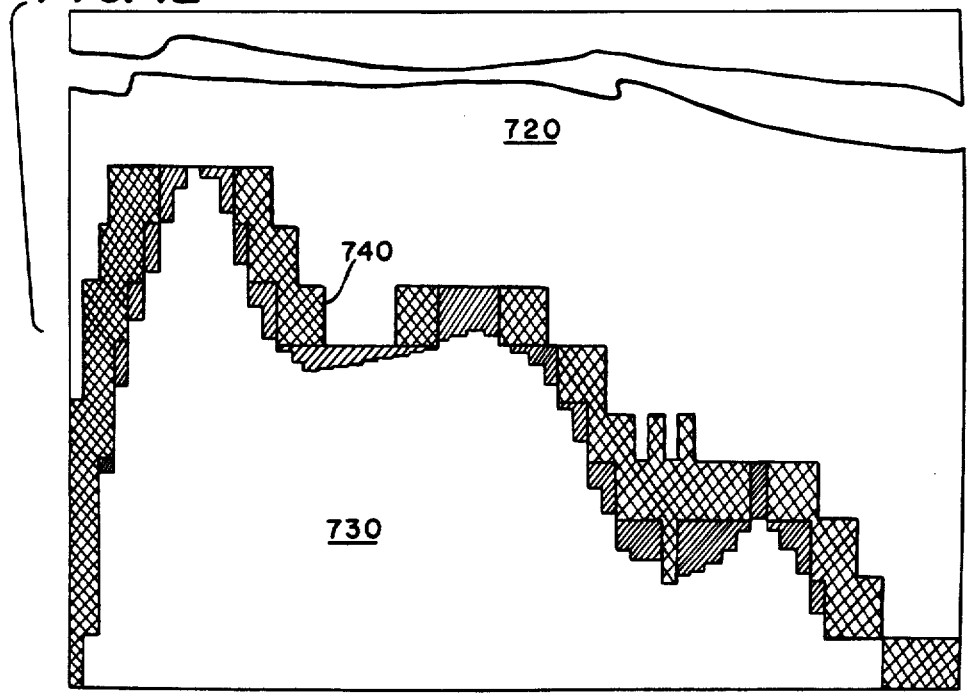

Referring to FIGS. 9, 10, 11 and 12, illustrations are provided of the active memory required for parameter signal storage, 730, utilizing the alternate data storage system wherein the white area 730 of the illustrations and the shaded (dark) areas represent the actively utilized memory locations utilizing the present invention. The cross-hatched regions 740 represent the overhead memory requirements for smaller word resolutions and white areas 720 represent the unutilized memory additionally required by conventional systems. FIG. 8 illustrates the 16 bit/word case. FIG. 9 illustrates the byte resolution case, where the word length equals one byte (8 bits). FIG. 10 illustrates the nibble resolution case, where a nibble is a four bit word length. FIG. 11 illustrates the two bit resolution case, where the word length is two bits per word. FIG. 12 illustrates the bit resolution case, where each data word is one bit word. The data base utilized in the preparation and presentation of FIGS. 7-12 is based upon empirical data gathered from use of a system embodying the present invention. Specifically, this data was gathered in accordance with a florescent activated cell sorter system, a FACS IV system, as commercial available from Becton Dickenson, modified in accordance with the present invention.

Referring to FIG. 13A, a flow chart for the linked matrix data compaction system and method of the present invention is illustrated. As discussed above herein, in the linked matrix embodiment of the present invention, a first memory forms a pointer matrix to a string of data counters in a second memory, pointed to by the pointers in the first memory. A pointer is created in the first memory only upon the occurrence of a particular combination of parameter signals, the pointer providing an address to one of the data counter locations of the second memory in which to store the accumulated count for the number of occurrences of the combination of parameters associated with the first pointer.

The data compaction and decompaction can be accomplished in conjunction with a programmable digital computer, or alternatively can be embodied in discrete hardware, such as digital logic or programmable logic arrays. As shown in FIG. 13A, the functional implementation starts with the function 1000 of initialization. Initialization includes assigning a starting address to the address pointer ADDPTR, assigning a default null value, assigning the null value to all the pointers, and clearing all count location planes, such as by storing 0 therein. The flow charts of FIGS. 13A and 13B correspond to the nibble count embodiment as described earlier herein, wherein the plurality of nibbles is associatively combined to form a single count value as needed. Upon completion of initialization, the input parameter signals are retrieved as shown at functional block 1010, after which point the nibble level is set equal to one as shown in functional block 1020. The upper and lower coordinates (subwords) of the address associated with the input parameters are calculated, as shown at functional block 1030, and the associated pointer with these calculated subwords of the input parameters is retrieved from the first memory matrix, as shown at function block 1040. This pointer value is checked for the null value, as shown at logical decision block 1050, to determine whether this combination of parameters represents the initial occurrence of the combination, requiring assignment of an address pointer value to the pointer location in the first memory matrix as shown at function block 1055, or is not the initial occurrence in which case the count value incremented, as commenced at function block 1070.

If the combination of input parameters represents the initial occurrence of said combination, the functioning of the system proceeds by assigning an address pointer value ADDPTR to the pointer at the location addressed in the first memory, as shown at logic function block 1055. This assigned pointer value is then stored in the location addressed by the subwords corresponding to the combination of input parameters within the first memory matrix, as shown by the function block designate 1057 for storing the pointer in the contents of the addressed location (U1, U2) of the first memory (of the N level pointer matrix).

The stored count value in the second memory count matrix is then incremented at the location corresponding to the pointer value from the first memory and the secondary subwords (L1, L2) of the associated address of the occurring parameters (as shown at function block 1060). Functioning proceeds from function block 1060 to function block 1065 where the address pointer ADDPTR is updated to a new value corresponding to an unused second memory location, and the address pointer and count value are checked for overflow. If no overflow occurs, functioning proceeds by returning to functional block 1010 and retrieving two new parameter signals.

Returning to logical decision block 1050, if the pointer retrieved from the first memory pointer matrix corresponding to the location addressed by the subwords associated with the occurring parameters address is not at the null value level, indicating a noninitial occurrence of the combination of parameters, then functional processing proceeds to function 1070. The count value stored in the second memory count matrix, as addressed by the pointer and the second subword of the address associated with the combination of parameters, (L1, L2) of the count matrix is retrieved from the second memory. The count is then incremented, as shown at function block 1080. The count value is checked for overflow, as shown at logical decision block 1090. If the count has not overflowed, functional processing proceeds by returning to function block 1010 where new parameters are retrieved, and processing proceeds therefrom as described above.

If the count value has overflowed at logical decision block 1090, processing proceeds to function block 1100, where the nibble level, NLEVEL is incremented. The NLEVEL value is then checked for being in bounds, the illustrated example being of a value 1 to 4. If NLEVEL equal 5, indicating the count exceeds the maximum allocated incremental nibble count, an error message is generated as shown at function block 1120, and functional processing is halted as shown at exit block 1130. If the incremented N level is at a legal level, less than 5, functioning proceeds from logical decision block 1110 to function block 1040, where a pointer is retrieved from the first memory matrix for NLEVEL as incremented, from the address corresponding to the subword, (U1, U2) associated with the parameter combination occurring. Processing proceeds herefrom as described above, preceding the logical decision block 1050, for determining whether this is the initial or noninitial occurrence of the parameter combination at this N level.

The functional description as provided above for FIG. 13A refers to the two level linked matrix compaction method and system of the present invention. As discussed above herein, the two level approach can be expanded to a three level approach, where the first pointer points to a number of level two matrices in an associated level two memory. The level two memory contains second pointers to locations in a level three memory which functions to store the accumulated count values. An advantage of the linked marix system and method over a conventional linked list technique is both reduced memory requirements and a reduction in the time required for dynamic allocation and address retrieving via the linkage pointers.

Referring now to FIG. 13B, a linked matrix data decompaction method and system is illustrated compatible with the compaction flow chart illustrated in FIG. 13A. Generally speaking, each potential parameter combination is sequentially asserted to associative address decode means which provides associated subwords, and the pointer values from the first memory pointer matrix are retrieved, evaluated, and utilized to access a count storage location in the second memory, if the pointer is not a null, and the various nibble levels (N level) counter locations are combined to form a total count value for that matrix element associated with a particular parameter combination. More specifically, referring to FIG. 13B, a parameter combination (channel 1, channel 2) is assumed and addressed to the first memory matrix, as shown in function block 1200. The upper and lower subword coordinates [(U1, U2), (L1, L2)] are calculated from the address associated with the parameter combination, as shown in function block 1210. The nibble level is set to 1 and the count set to 0 for the combination to initialize the decompaction system, as shown at block 1220. The pointer value is then retrieved from the first memory pointer matrix location (as addressed by subword U1, U2), as shown at function block 1230. If this pointer is equal to a null value, indicating no occurrences of the associated parameter combination, the count value is assigned the current count value, in this case initially 0, for the value of the matrix element associated with the asserted combination of parameters, as shown at function box 1290, and functional processing proceeds returning to function block 1200 to access the next parameter location. Alternatively, if the pointer value retrieved at functional block 1230 is determined not be null, indicating that the parameter combination associated with the pointer has occurred at the present N level, processing proceeds from logical decision block 1240 to the functional decision block 1250.

The stored count value (X) in the second memory count matrix is retrieved from the location addressed by the second subword (L1, L2) of the plane of the second memory pointed to by the associated pointer. The count value is assigned the value of the present count value plus the retrieved count value from the present N level times 16 raised to the power of the present level minus 1, as shown at functional block 1260. The present N level is then incremented, as shown at function block 1270, and the new value is tested as to whether the number of levels present in the illustrated system is exceeded, in this case four levels, as shown at logical decision block 1280. If the level is greater than four, indicating all N levels have been accounted for, then the value of the matrix element associated with the presently asserted parameter combination is assigned the present COUNT value, as shown at function block 1290, and functional processing proceeds by retrieving the next combination of parameters, at function block 1200. Alternatively, if the incremented NLEVEL is determined, at logical decision block 1280, to be less than or equal to the predefined maximum number i.e., 4, then processing proceeds to get the pointer from the current NLEVEL pointer location within the first memory as addressed by the subword associated with the presently occurring combination (U1, U2), at function block 1230. Functional processing proceeds from here as described above, first testing to see if the newly retrieved pointer value is a null, a logical decision block 1240. If it is a null, indicating no occurrence of the combination at this N level, the presently accumulated count value is the total count value for this matrix element, and processing proceeds to functional block 1290 where the count valued is stored as the value of the matrix element, and functioning proceeds back to block 1200. Alternatively, if the pointer value for this N level is not a null, processing proceeds to functional block 1250 and therefrom as described above.

The linked matrix data decompaction method as described with reference to FIG. 13B is compatible with the compaction method described with reference to FIG. 13A. In this regard, the data decompaction method of FIG. 13B is related to the two level linked matrix compaction and decompaction method and system. Alternatively, a three level compaction and decompaction method and apparatus can be implemented, as discussed at numerous places above herein. The linked matrix method and apparatus can be used with any array, including images such as CAT Scan, NMR, weather satellite photographs, etc. either for file compaction or as a real time memory saver. The choice of pointer matrix size is not fixed, and various divisions can be tried to find an optimum value. Additionally, the size of the counter memory locations can be other than four bit nibbles. As discussed with reference to FIGS. 8 to 12, 16 bit, 8 bit, 4 bit, 2 bit, or even 1 bit counter memory locations can be utilized, in either individual or incremental count structures. Alternatively, the count resolution of various incremental groups need not be uniformly divided. Thus, the first count incremental level could utilize one or two bits, with 4 to 8 bits at higher levels. This type of incremental count technique, however, requires adjustment of the first memory pointer matrix sizes for respective NLEVEL groups, so as to allow the pointers to point to uniformly sized count plane. Thus, for the example of four counter planes and four pointer planes, the level one pointer plane could be an eight by eight word matrix pointing to a thirty-two by thirty-two matrix of one bit counters, the level two pointer matrix could be a sixteen by eight word matrix pointing to a sixteen by thirty-two bit counter plane, the third level of pointer matrix could be a sixteen by sixteen word pointer matrix pointing to a sixteen by sixteen four bit counter plane, and the fourth level of pointer matrix could be sixteen by thirty-two words pointing to a sixteen by eight eight bit count word plane. Utilization of nonuniform incremental groupings results in different memory requirements from that of the uniform scheme as illustrated in FIGS. 13A-B.

In accordance with another aspect of the linked matrix compaction and decompaction method and apparatus of the present invention, a limited size count memory could be utilized to continue storing count data even after memory space in the count memory is full. When all the counter memory space is full, a control means could reclaim locations in the counter memory planes where the count activity is below a predefined minimum, thereby freeing that memory space for additional counting. However, since some data is lost in this scheme, this type of function is better implemented as an operator option, rather than as a standard feature.

In still a further embodiment of the linked matrix compaction decompaction method and apparatus of the present invention, memory space in the counter memory could be saved by utilizing a dynamic adjustment technique wherein the size of the counter planes are dynamically adjusted such that sparse regions are assigned smaller data planes, and denser regions are assigned larger data planes.

In accordance with the alternate system embodiment of the present invention utilizing an encoding system with an embedding technique in a single memory, data could be screened onto a disk or tape in real time, and then compacted, off line, for one or plurality of dimensions. In accordance with this embodiment of the present invention, storage requirements are reduced by storing the incremental address (the increment from a previous address to the present address) rather than the absolute address associated with a parameter or combination of parameters occurrence count. A normal increment of address can be assumed, such that the default condition is an assumption of the normal increment value and only a count value need be stored where the increment is the normal increment.

Where, however, the address increment is larger than the normal increment size, then a flag count word can be utilized as a signal that a multibyte or multiword incremental address is to follow. For example, the next byte of stored data could be defined as the lower byte of the multibyte incremental address. To optimize the amount of compaction resulting from this alternate embodiment of the present invention, an N by N data base, already sorted by the nature of the file, can be taken as a sample, a histogram made of the count values, an optimum bit length for the count word chosen, and the effect of various count word lengths on total storage could be estimated. This same technique could be utilized with address increments to choose or estimate the optimum word size for address increments.

For example, an analysis of an actual 64×64 data base showed that 340 of 4096 addresses were actually occupied with data, and that all but 30 address jumps were plus 1 increment. Thus, for this example, it is useful to assume an address increment of plus 1 unless the stored data word flags a unique count word which signals a larger address increment. Otherwise, the stored value is assumed to be the count value for the next incremental address. In this way, data storage requirements are reduced as compared to the technique of storing the address and associated count value for each address. Additionally, where the count value exceeds the allocated storage word size, a unique count word could flag a multiple word count value for the associated address. In part, the savings of storage space occurs because the data tends to be of a grouped nature, and thus, storage space can be saved by sorting the list organized data by group numerical order, and then adding a tag byte to indicate the frequency of an event (group). By using an assumed address increment, and address increments instead of absolute addresses, even further storage savings are realized. One technique is to use an incremental offset where for a one byte incremental address, the first byte of a pair is an incremental address, and the next byte is the count value for that address. Where the offset is greater than can be indicated in a single byte, the count byte associated with the first address byte of the incremental address can be made to equal zero, or some other predefined value, to signal a multibyte incremental offset. In a similar manner, a multiple byte count can be indicated by making subsequent incremental address offsets equal to zero, or some other predefined value.

This technique is illustrated in the flow charts of FIGS. 14A-D. Referring now to FIG. 14A, a specific implementation of the alternate system embodiment is shown. Data compaction utilizing the embedded count and offset method proceeds as follows. Starting at entry point 2000, system variables are initialized. The variables which are initialized can include the full scale values for the address increment, count, as well as initialization of the memory pointer, and definition of special flag words. The first stored count value is read, as indicated at functional box 2020, after initialization of variables. This count value is compared to zero, as indicated at logic decision block 2030. If the count is not zero an initialized flag is tested to see if the system is in the address jump mode, as indicated at decision logic block 2040. If the system is not in the jump mode, then the read count value is stored, as indicated in function box 2300, which is further detailed in FIG. 14C, as will be discussed hereafter. After the count value is stored, processing proceeds by returning to read the next count value at function block 2020. If, however, decisional logic block 2040 has determined that the system is in the jump mode, then processing proceeds to function block 2050 which causes the system to enter the store mode and to proceed to function block 2200 to store the address jump offset (AJUMP), as shown in greater detail in FIG. 14B, to be described hereafter. After storing the address jump offset, processing continues by proceeding to store the count value, as detailed at function block 2300 and at FIG. 14C, after which point processing proceeds back to read the next count value as shown at function block 2020. Returning to logic decision block 2030, if the read count value is equal to 0, processing proceeds to logic decision block 2070 which determines if the system is in the jump mode. If it is determined that the system is in the jump mode, then the present jump address value is incremented (AJUMP=AJUMP+1) as shown at function block 2080, and processing proceeds to read the next count value, as indicated at function block 2020. Alternatively, if there was determined, at logic decision block 2070, that the system is not in the jump mode, then it is next determined whether the present word is finished, as illustrated at logic decision mark 2090. If it is determined that the present word is finished then processing proceeds to the assign the address AJUMP word equal to one, and to enter the jump mode, as shown at function blocks 2130, and 2140, respectively, from which point processing proceeds to read the next count value as shown in the function block 2020. If, however, it is determined that the present word is not finished, then processing proceeds to function 2100, to fill the low byte of the present word with 0, and to store the word at the location indicated by the address pointer (high, low) as shown at function block 2110. Thereafter, the address pointer value is incremented (high, low) as shown at function block 2120, the address AJUMP value is signed equal to 1, the system is caused to enter the jump mode, as shown at function blocks 2130 and 2140, respectively, and processing proceeds to read the next count value at function block 2020.

As shown in FIG. 14A, at function block 2200, where the count value is not equal to 0 and the system is in the jump mode, the system is caused to enter the store mode, and to store the AJUMP value. Referring to FIG. 14B, the flow chart for the store AJUMP function block 2200 is shown in expanded form. Upon entry at 2205, the high byte of the address point is assigned equal to 0, at function block 2210, and AJUMP is tested to see if it is within allowable bounds, i.e., in the illustrated figure less than or equal to 247. If it is determined, at logic decision block 2210, that the AJUMP value is greater than 247, then the low value of the address pointer is set equal to 255 (its maximum value for a byte word), at function block 2260, the AJUMP value is stored at the location addressed by high, low, as shown in function block 2270. The address pointer high, low is incremented, as shown in function block 2280, the value of AJUMP is reduced by the predefined value (247), as shown at function block 2290, and processing proceeds to decisional function block 2220 to determine if AJUMP is less than or equal to or greater than the predefined value 247. If, however, instead of determining that AJUMP was greater than 247, it is determined that AJUMP is less than or equal to 247, and processing proceeds to function block 2230 and thereform. At function block 2230 the low byte of the address pointer word is assigned equal to address jump plus 8, to offset and compensate for reserved flag bytes of the AJUMP word. The AJUMP value is then stored at the location pointed to by the address pointer (high, low). The address pointer (high, low) is then incremented, as shown at function block 2250, and processing proceeds to function block 2300 of FIG. 14A, to store the count value, as detailed and expanded in FIG. 14C.

Referring now to FIG. 14C, a flow chart for the store count function 2300 is shown. Upon entering at 2305, an initial determination is made whether the count value is greater than 255, at logic decision block 2310. If the count is greater than 255 (the maximum value of a byte count word), then the count is compared to 64K (65,526) (the maximum value of a 16 bit count word), as shown at logic decision block 2460. If the count is greater than 64K, an error message is issued as shown at function block 2470, and the system exits from the processing as shown at function block 2480. If the count value is determined greater than 255 but less than 64K, then processing proceeds by the logical determination of whether the system is in the double byte mode and determined at logical decision block 2490. If the system is in the double byte mode, then the high byte equals the integer value of the count divided by 256, and the low byte of the count word is set equal to the total count minus 256 times the high byte value, as shown at function block 2580. Processing then proceeds to return to the count value fetch function block 2020 of FIG. 14A. Alternatively, if it is determined at logic decision block 2490 that the system is not in a double byte mode, then it is next determined whether the present word is finished, at function block 2500. If the present byte is not finished, then the low byte of the address pointer is said equal to 0, and the word is stored at the location pointed to by the address pointer (high, low). This is shown at function blocks 2510 and 2520, respectively. The address pointer (high, low) is then incremented as shown in function block 2530, and the high byte is said equal to 0 to indicate a double byte, and the low byte is said to equal to 2 to indicate the double byte mode, as shown at function block 2540. Alternatively, if it is determined at logic decision block 2500 that the present word is finished, then processing proceeds directly to 2540, skipping function blocks 2510, 2520, 2530, such that the high byte is set equal to 0, no low byte is set equal to 2 to indicate the double byte mode. From function block 2540, processing proceeds to function block 2550 where the count value is stored at the location pointed to by the address pointer (high, low). The address pointer is then incremented, as shown at function block 2560, and the system is set to the double byte mode, as shown in function block 2570. The value of the high byte is then said equal to the integer value of the count divided by 256, and the low byte value is said equal to the count minus 256 times the value of the high byte, at function block 2580, and processing returns to retrieval of the count value at function block 2520 of FIG. 14A, as previously discussed. Returning to logical decision block 2310, if upon entry to the store count routine, it is determined that the count value is less than 255 or equal to 255, then a determination is made whether the count value is less than 0, at logic decision block 2320. If the count is less than 0, then an error message is issued, at 2330, and the system exits from the store count procedure, as shown at 2340. Alternatively, if the count is determined to be less than or equal to 255, and greater than or equal to 0, then the logical decision is made at block 2350 whether the system is in the double byte mode. If the system is in double byte mode, then the high byte is set equal to 0 and the low byte is set equal to 1, indicating the single byte mode, as shown in function block 2410, the count value is stored at the location addressed by the address pointer (high, low), and the address pointer is incremented, as shown at function blocks 2420 and 2430, respectively. The high byte is then said equal to count, the present word is set to unfinished, as shown at function blocks 2440 and 2450, respectively, and processing continues by retrieving the next count value, as shown in function block 2020 of FIG. 14A. Alternatively, if upon entry to the store count routine, is determined that the count value is less than or equal to 255, and if the count is greater than or equal to 0, and that the system is not in the double byte mode, it is next determined whether the present word is finished at logic decision block 2360. If the present word is finished, processing proceeds by setting the high byte equal to count (HI=COUNT), as shown in function block 2440, and the present word is designated unfinished, as shown in function block 2450, with processing continuing at function block 2020 of FIG. 14A, by retrieving a new count value. Alternatively, if at logic decision block 2360 it is determined that the present word is not finished, then the low byte (low) said equal to the count, as shown in function block 2370, and the count value is stored at the location pointed to by the address pointer (high, low), as shown in function block 2380. The address pointer is incremented (high, low), as shown in function block 2390, and the present word is set as finished, as shown at function block 2400. Processing then proceeds to retrieve the next count value, as shown in function block 2020 of FIG. 14A.

In other words, it is assumed that all data is stored as 2 bytes or 16 bit words, consisting of a high and low byte. The maximum count is also assumed to be equal to 2 bytes equal 64K. A double byte flag is initialized and modified during processing of the system. Each of the 2 bytes of the 16 bit data word functions as both a data word and a flag word. Thus, if the most significant byte is equaled to 0, the least significant byte is a function flag. Alternatively, where the least significant byte is 0, the most significant byte can be determined as a function flag. Thus, if both bytes are 0, the word is skipped over. Alternatively, if then first byte is less than 256 and greater than 0, the 2 counts are packed into one word, each count being one byte. This is but one of various schemes that can be implemented in accordance with the present embodiment of the subject invention. Additionally, separate double precision flag, byte 1 and byte 2 ready flags, and predefined maximum count and address values can be assigned and initialized by the system, separate from the actual stored and retrieved count and data values.

Referring to FIG. 14D, the byte decompaction method of the present embodiment of the alternate system embodiment of the present invention is shown, compatible with the compaction method illustrated in FIGS. 14A–C. Starting at 2601 and proceeding to function box 2602, the contents of the high and low bytes of the stored data word are read. If the high byte is equal to 0, as determined at logic decision block 2610, then the low byte is tested. If the low byte is greater than 8, as determined at logic block 2700, then the address is assigned equal to the address plus the low byte minus 9, and a determination is made as to whether the end of file has been reached, as shown at function block 2710 and decision block 2720, respectively. If the end of file has been reached then the system exits from the decompaction routine, as shown at function 2730. Alternatively, if the end of file has not been reached, the functioning resumed, starting over at entry point 2601. Alternatively, if the high byte is determined equal to 0, at logic block 2610, and the low byte is less than 8, as determined at logic decision block 2700, then the low byte is tested for being equal to 1 (logic block 2740, in which case the system is forced to enter the single byte mode, as shown in function block 2790, while if not equal to 1 the low byte is tested to be equal to 2, at logic decision block 2750, in which case the system is forced to enter the double byte mode, as shown at function block 2760. Upon entering either the single byte mode at function block 2790 or the double byte mode at function block 2760, the system proceeds to return to the start entry point 2601 of the decompaction algorithm. If, however, it is determined that the high byte is equal to 0, and the low byte is not greater than 8, but is not equal to 1, and is greater than 2, then an error message is generated as shown at function block 2770, and the system exits from the decompaction algorithm, as shown in function block 2780. Returning to logic decision block 2610, where the high byte is determined to not be equal to 0, functioning proceeds to determine if the system is in the double byte mode, as shown in logic block 2620, in which case the count value is said equal to 256 times the high byte value plus the low byte value, as shown in function block 2800, the address is incremented, as shown at function block 2810, and the address is tested for end of file, as shown at logic block 2820. If at the end of file, the system exits from the decompaction algorithm as shown in function block 2830. Alternatively, if the system is not at the end of file, then the system proceeds to return to reenter the decompaction algorithm at entry point 2601. Returning again to decision logic block 2610, if it is determined that the high byte is not equal to 0, and that the system is not at a double byte mode, at logic block 2620, then the count is said equal to the high byte, as shown at function 2630, the address is incremented, as shown in function block 2640, and the low byte is tested for 0 value, in which case processing returns to the entry point 2601 of the decompaction algorithm. If the low byte is not equal to 0, then the count is said equal to the low byte, as shown at function block 2660, the address in incremented, as shown in block 2670, and the count value is tested for end of file. If end of file is determined, then the system proceeds to exit from the decompaction algorithm as shown at function block 2690. If not end of file, then the system proceeds to reenter the decompaction algorithm at entry block 2601.

As discussed with reference to FIGS. 14A-D, byte or multiple byte word storage has been discussed. However, the storage word length can be varied, with multiple words being utilized for exceptionally long count values or address increments. Alternatively, the length of the word to be utilized to indicate a count or jump value can be indicated by means of a preceding flag and data values. For exmaple, with normal words, a 0 first nibble flag, the value of 3 indicating the jump word length follows, the second nibble could indicate the number of values in the jump word for example as two bits by a 0 value, 4 bits by a 1 value, 6 bits by a 2 value or could indicate a greater number of bits by a 3 value, indicating that the next following nibble would indicate the total value, for a 0 in the next nibble would indicate 8 bits, a 1 would indicate 10 bits, 2 would indicate 12 bits, etc. The actual assignments made could be made to reflect the most frequently utilized jump instruction length. These are of course but a few of the alternate techniques which can be utilized in accordance with this alternate system embodiment of the present invention.

FIGS. 15A-C correspond to a specific computer program implementation of the compaction flow charts of FIGS. 14A-C. FIG. 15D is a flow chart of a specific embodiment of the decompaction flow chart of FIG. 14D.

Utilizing this technique a great savings in memory storage requirements to log count and associated physical address is achieved. For a total count of cells of 200,000, the conventional list mode would require approximately 2 bytes per cell or 400,000 bytes. Alternatively using the pact embedded embodiment of the present invention only 596 bytes would be required, 256 plus 256 plus 84 equals 595 bytes. Thus, a factor of 500 savings is achieved. The savings was achieved utilizing a byte oriented scheme, as illustrated in FIGS. 15 and 16, while a nibble oriented scheme would result in even a greater savings.

Implementation of this embodiment of the system invention totally in hardware could proceed according to the same flow diagrams. However, by their nature, the compaction and decompaction operations require careful attention to timing, as the data input and output rates must be different. Alternatively, the present invention can be utilized in conjunction with some hardware and a programmed digital computer to overcome many of the timing problems, or can be implemented, as discussed above, in conjunction with a FACS IV (flurescent activated cell sorter) system, modified in accordance with the teachings herein, to achieve the memory storage savings and benefits of the present invention.

As discussed herein above, the present invention can be utilized in many diverse fields of application, in both scientific and statistical applications. One embodiment of the present invention has been implemented in the field of cellular tissue analysis (Cytology) in conjunction with a commercially available electronic system, commercially available as the Becton Dickenson FACS IV, a fluorescent activated cell sorter. By way of background, the FACS IV system separates cells on the basis of fluorescence and size using principles developed by various persons at Los Alamos and Stanford. The separation is accomplished by confining cells of interest to the center of a liquid stream and causing them to pass one at a time through the focused beam of a high-power laser. Each cell is characterized by the amplitude of the signals corresponding to the intensity of the light scattered by the cell and by the intensity of fluorescence emitted while it is in the laser beam. These signals are processed by the instrument, which then determines whether they meet certain operator-selected criteria. If they do, the cell is identified as one that should be separated from the other cells within the stream, and directed into an appropriate container. Separation is achieved by passing the liquid stream through a small nozzle that is ultrasonically excited, causing the stream to form regularly spaced, equal-volume droplets. The droplet containing the cell of interest is electrically charged and then deflected by passing it through an electric field. This separates the droplet—and and the cell contained within it—from the main stream and allows it to be collected in a suitably placed container.

The availability of the FACS instrument brings a new dimension to cytology by making it possible to analyze large numbers of cells quantitatively, and to verify the results of that analysis by subsequent examination of separated cell fractions. This closed loop—analysis, separation, and verification—makes possible rapid improvements in the art of cell analysis and at the same time provides purified fractions for subsequent experimentation. Applications include general immunology, cancer research, chromosome analysis and cell-cycle analysis.

When changes and improvements are required, the open, modular construction of the optical bench and fluid handling subsystem allows rapid retrofitting of new hardware items. When required, an interface can be supplied to connect the data analysis system of FACS to an external computer, to allow further manipulation of data.

As discussed elsewhere herein, one problem faced in utilizing the FACS IV system is the limited data memory storage. When multiple parameters are analyzed, and data is stored utilizing conventional techniques, the memory becomes a limiting factor in the cell concentration levels, the number of resolution levels, and the number of parameters which can be sampled and analyzed. Even with the connection of an external computer to the FACS IV system, the memory requirements can be a limiting factor. It is in this regard that the application of the present invention is beneficial, increasing the capabilities and uses of the FACS IV system. However, the same benefits accrue to any system which correlates and analyzes large numbers of data samples.

A detailed technical description of the electronic, optical, and medical aspects of the FACS IV cell sorter system is presented in Chapter 37 of a book entitled *Flow Cytometry and Sorting*, edited by Myron R. Melmed, Paul F. Mullaney, and Mortimer L. Mendelsohn, published by John Wiley and Sons, copyright 1979. Chapter 37 is entitled "The Becton Dickinson FACS IV Cell Sorter", authored by Mack J. Fulwyler, Capers W. McDonald, and John L. Haynes, at pages 653 to 667 of the book. Chapter 37 of the book detailing the FACS IV system is hereby incorporated by reference herein. Additionally, several brochures, and manuals on the FACS IV system are available directly from Becton Dickinson of Paramus, N.J.

The benefits accruing from utilization of the present invention with the FACS IV system can be or easily understood by presentation here of a brief discussion and description of the operation of the FACS IV instrument. A block diagram of the various components of the FACS IV system is shown in FIG. 17.

During an experimental run, sheath and sample liquids are held in pressurized containers 4010, 4020, respectively, which may themselves be held in a temperature-controlled water bath. Suitable adjustment of the air pressure in the sample and sheath containers allows a sample of fluorescently tagged cells to be injected into the center of a flowing stream of compatible sheath liquid, usually identical to the medium in which the cells are suspended, in fluid valve 4030 thereby establishing a laminar coaxial flow within a nozzle-transducer assembly 4040.

The coaxial flow will constrain the sample fluid, and the cells contained therein, to the central portion of the liquid flow stream, giving accurate positioning in the laser beam 4000. The stream, after emerging from the nozzle tip, is about 50$\mu$ in diameter, and continues in an unbroken jet for about 1.8 mm, after which perturbations within the flow stream induced by means of a 40-kHz piezoelectric transducer upon which the nozzle is mounted, build up and cause the stream to break up into well-defined, constant-volume droplets, 4050.

Immediately below the nozzle 4040 and before being formed into droplets, the stream is interrogated by a laser beam 4000 and optical detectors 4070 to ascertain the presence of cells and their characteristics.

In general, as cells pass through the laser beam 4000, different cells will generate different but characteristic signals, both in fluorescence and in scattering. These differences manifest themselves as variations in the intensity of the light from each cell, which in turn are converted into electrical pulses of varying amplitudes by the photodetectors 4070.

The scatter signal is detected by observing the illumination in the forward direction, that is, by looking at the cell when it is in line with the laser beam.

The fluorescence characteristics of the cell are determined simultaneously with the scatter signal. Cells that have been dyed or tagged by means of a suitable fluorescent material can be detected by means of their emission when excited by the laser at a suitable wavelength of light.

As it passes through the laser beam, a cell is detected by a characteristic scatter signal, and by one or two fluorescence signals, should they be generated. These optical signals are converted into electrical signals by suitable photodetectors, and the electrical signal are then processed by the electronics portion of the system. First, the signal pass through individual low-noise, variable-gain amplifiers 4080 that allow the operator to adjust the pulses until they are up to eight Volts in amplitude, as determined by observing them on an oscilloscope display built into the instrument. From there they are taken to a pulse-height analyzer 4100, where the pulses are recorded and presented to the operator for evaluation and analysis.

When functioning as a pulse-height analyzer (PHA), the FACS IV data analysis system measures and counts electrical pulses that have amplitudes varying from zero to about eight Volts. An analog-to-digital converter is used to divide this eight-Volt span into many small increments called channels. An individual count totalizer, capable of recording a million events, is assigned to each channel. Whenever a pulse is presented to the PHA, its amplitude is measured and a count is added to the appropriate channel count-totalizer. As a train of pulses of varying amplitudes is presented to the PHA, each pulse is individually measured and the total number at each digital measurement increment is stored in its corresponding count-totalizer. The PHA display presentation, called a pulse-height distribution or histogram, is a graphic representation of channel number (as the abscissa) and counts (as the ordinate).

Because the cell-sorter optical sensors produce electrical pulses corresponding to variations in physical characteristics of a cell population, the pulse-height distribution observed relates directly to the distribution of those characteristics within the total population.

PHA data accumulation can be in a single parameter mode or in a dual mode where data can be simultaneously collected from any two of the parameters available. In the two-parameter mode, the PHA can simultaneously collect and display information from any two of the available parameters. Two forms of dual parameter data acquisition are available. In uncorrelated data acquisition the two measurements associated with a cell are processed separately, and correlation is not made. Selection of the uncorrelated, or side-by-side data acquisition results in two discrete curves which can be displayed.

In correlated data acquisition the two measurements associated with a cell are processed in parallel, and correlation of the measurements for each cell is made. The correlated, or "X-Y," form of dual parameter acquisition collects the data as a matrix of 64×64 channels. The correlated two-parameter data can be displayed as a 64-channel profile pair, or in the correlated isometric and contour forms shown in FIG. 7. In the contour and isometric modes, it is also possible to display only the data channels above an operator-selected COUNT threshold. In the FACS IV system, auxiliary electronic measurement devices, 4090, (analog-to-digital converters) to measure up to four separate parameters associated with each cell, including the ratio of any two parameters.

An electronic functional block diagram is illustrated in FIGS. 18A and 18B, further detailing the block diagram of FIG. 17.

Referring to FIG. 16, a pictorial illustration of the FACS IV apparatus is shown. The FACS IV instrument system is comprised of two units, an electronic control and display console 5000, and an optomechanical unit 5010 consisting of an optical bench and fluid flow assembly. Selection of window combinations for analysis and sorting, and selection and routing of all data used and generated by the instrument are controlled by appropriately grouped switches and indicated on the electronic control and display console 5000. The sorting, detection, amplification and filtering functions are performed by the optical bench and fluid flow assembly apparatus 5010.

While the present invention has been described with reference to specific embodiments, it will be understood to those skilled in the art that these embodiments are given for illustrative purposes, and should not be construed in a limiting sense. Having described in detail various embodiments of the present invention, it will now be apparent to those skilled in the art that numerous modifications can be made therein without departing from the scope of the invention as defined in the appended claims.

What is claimed is:

1. A data storage system for storing in a digital memory the number of occurrences of each possible combination of values for a group of parameters, wherein each parameter can have a predefined number of values and wherein the occurrences of the parameter combinations are input as sequential sets of values together forming a data base, said storage system comprising:

means for receiving each occurrence of a parameter set and for generating parameter set addresses, each parameter set address corresponding to a particular combination of parameter values received;

a first memory segment having a plurality of pointer locations corresponding to a predefined group of parameter sets of said data base;

a second memory segment having a plurality of count locations for storing count values indicative of the number of occurrences of a particular parameter set in the data base sequence;

means for assigning a data area of said second memory segment count locations for the storage of the occurrences of one group of said parameter sets in response to the first occurrence of one parameter set in the parameter group, said data area having count locations corresponding to each parameter set of a parameter group;

means for associatively linking said first memory pointer locations and said second memory data areas by storing a pointer address indicative of said assigned data area in a pointer location of said first memory corresponding to the parameter group containing a presently occurring parameter set of the sequence;

means for determining the count location corresponding to said presently occurring parameter set by decoding said set address and said pointer address; and means for incrementing the count value stored in said determined count location corresponding to the presently occurring parameter set.

2. A data storage system as defined in claim 1 wherein said second memory locations are of a fixed bit length and can store a maximum occurrence count determined by that length, said system further comprising:

means for determining whether incrementing the count location corresponding to the presently occurring parameter set will cause the occurrence count stored therein to exceed said maximum occurrence count and for generating an overflow signal indicative of the presence of such condition;

wherein, in response to said overflow signal, said assigning means assigns another data area to said group of parameter sets and said associative linking means stores another pointer address indicative of said another data plane in the pointer location of said first memory corresponding to the parameter group of the presently occurring parameter set; and wherein said determining means determines the count location in said another data plane corresponding to the presently occurring parameter set by decoding said set address, said pointer address, said overflow signal, and said another pointer address.

3. A data storage system as defined in claim 1 wherein:

said parameter group contains only one parameter set element.

4. A data storage system as defined in claim 1 having a first parameter with a number values P and having a second parameter with a number of values Q wherein:

said parameter set address generating means generates a first parameter address as a digital word having a bit length of $\log_2 P$ and generates a second parameter address as a digital word having a bit length of $\log_2 Q$.

5. A data storage system as defined in claim 4 wherein:

said first memory is addressed by (a) higher order bits of said first parameter address and by (c) higher order bits of said second parameter address; and said assigned data area is addressed by (b) lower order bits of said first parameter address and by (d) lower order bits of said second parameter address;

where $2^{a+b}=P$ and $2^{c+d}=Q$, such that said first memory pointer locations define $2^a \times 2^c$ parameter groups each having $2^b \times 2^d$ parameter sets.

6. A data storage system for storing in a digital memory the number of occurrences of each possible combination of values for a group of parameters, wherein each parameter can have a predefined number of values and wherein the occurrences of the parameter combinations are input as sequential sets of values together forming a data base, said storage system comprising:

means for receiving each occurrence of a parameter set and for generating parameter set addresses, each parameter set address corresponding to a particular combination of parameter values received;

a first memory segment having a plurality of memory locations, wherein each of said memory locations is divided into an address location and a count location;

means for assigning said memory locations in a sequence to particular parameter sets in response to the first occurrence of said parameter set, said assigning means storing the parameter address corresponding to said parameter set in the address location of the assigned memory location;

means for incrementing the count location of an assigned memory location in said first memory segment which corresponds to a presently occurring parameter set in the data sequence;

said first memory containing a linked list of parameter set addresses and count values in said memory locations.

7. A data storage system as defined in claim 6 which further includes:

a second memory segment having a plurality of memory locations, wherein each of said memory locations is divided into an address location and a count location; said second memory segment having smaller address and count locations than said first memory segment for compacting said linked list stored in said first memory;

means for reading the contents of said address locations and count locations of said first memory;

means for determining the difference between two sequential parameter set addresses thereby generating an incremental address representative of the address distance from one parameter set address in the list to the next;

means for replacing each parameter set address in said list with its associated incremental address;

means for storing each incremental address and corresponding count value in sequential memory locations in said second memory;

said storing means storing an increment flag word in the corresponding count location, if said increment address is of a greater length than said second memory address location, and storing said incremental address in consecutive address locations; and said storing means storing an a count flag word in the corresponding address location, if said count value is of a greater length than said second memory count location, and storing said count value in consecutive count locations.

8. A data storage system as defined in claim 7 wherein:

means for analyzing said linked list to determine the address location length and the count location length providing maximum data compaction; and said memory locations of the second memory are said determined lengths.

9. A data storage system comprising:

means for providing a plurality of individual parameter signals;

means for selectively providing an active set signal from a plurality of set signals, each of said set signals corresponding to a cross-correlated combination of said parameters;

a first memory having a plurality of storage locations addressable responsive to corresponding signals;

control means for storing, in said first memory, a plurality of first pointer signals respectively associated with each of said active set signals, responsive to the initial occurrence of said set signal;

a second memory having a plurality of storage locations addressable responsive to said first pointer signal; and a respective active set signal; and means for storing an accumulated count for the number of occurrences of each active set signal in a respective location in said second memory responsive to said first pointer signal and said respective active set signal.

10. The system as in claim 9 further comprising:

means for grouping sets of adjacent first memory locations into singularly addressable subgroup equivalent locations such that each first pointer signal corresponds to a subgroup address;

wherein said control means is further characterized in that one of said first pointer signal corresponds to all set signals within a common subgroup;

the system being further characterized in that said particular location in said second memory for storage of said accumulated count is selected responsive to said first pointer signal and its associated subgroup address.

11. A data logging system comprising:

a plurality of parameter signals each having a plurality of resolution levels;

a first matrix memory having a plurality of addressable locations;

means for associating particular first memory address locations with a particular combination of cross-correlated parameter signals and resolution levels, such that each such combination is associated with a single addressable location within the first memory;

means for providing a first pointer to an unused second memory address for storage in a selected first memory location responsive to the initial occurrence of a corresponding combination;

a second memory comprising a plurality of counter memory matrices, each counter memory matrix comprising a plurality of counter memory locations, each of said counter memory matrices being addressable responsive to a respective first pointer; and means for accumulating and storing count data representative of the frequency of occurrence of a respective combination responsive to said second pointer and said combination.

12. The system as in claim 11 wherein said first memory is further characterized as comprising a plurality of partitioned groups of pointer locations, and wherein said second memory is further comprised of a plurality of partitioned groups of counter locations for storing combination occurrence counts on an incremental basis, wherein each of said groups of pointer locations is associated with and addresses points to a respective group of counter locations in said third memory; said system further comprising:

means for detecting the overflow of a counter location;

means for providing and storing a first incremental pointer in the first memory at a location within a group of the next higher group level of that associated with the overflowed counter location group, said first incremental pointer addressing a counter location in the next incremental group relative to the group of the overflowed counter location in said second memory.

13. The data logging system as in claim 11 further comprising:

a third matrix memory comprising a plurality of sub-matrices;

means for providing a second pointer for storage in a selected matrix of said third memory responsive to the initial occurrence of the associated corresponding combination;

wherein each of said counter memory matrices is addressable responsive to a respective second pointer, and wherein said means for accumulating and storing count data representative of the frequency of occurrence of a respective combination responsive to said second pointer and said combination.

14. A data storage system comprising:

a first memory containing active parameter signals in selected locations and inactive data signals in all other locations;

a second memory, smaller than said first memory, having a plurality of storage locations;

means for storing all of said active parameter signals from said first memory in locations in said second memory associatively linked to respective physical locations of respective active parameter signals in said first memory, said associately linked second memory locations storing linking values indicative of the incremental distance between one active parameter signal and the next active parameter signal such that inactive parameters signals are discarded.

15. The data storage system as in claim 14 wherein said means for storing is further comprised of:
   means for providing a first signal for storage in a first location in said second memory responsive to a respective first active parameter signal wherein said first signal is a count signal having a value greater than a predefined threshold and responsive to said active parameter occurring in a fixed incremental location relative to the immediately preceding active parameter location in said first memory,
   means for providing a second value for storage in said first location in said second memory, responsive to said respective active parameter signal occurring in a fixed incremental location relative to the last preceding active parameter signal, and said respective active parameter signal having a value less than a first level,
   means for providing a third value for storage in said first location in said second memory responsive to said respective active parameter signal occurring in a fixed incremental location relative to the last preceding active parameter signal, and said respective active parameter signal occurring in a fixed incremental location relative to the last preceding active parameter signal, and said respective active parameter signal having a value greater than said first value;
   means for storing a fourth value in a second memory responsive to said third value and said respective active parameter signal, said fourth value being representative of a linking offset for combining with said third value to provide a complete representation of the parameter signal value.

* * * * *

UNITED STATES PATENT AND TRADEMARK OFFICE
CERTIFICATE OF CORRECTION

PATENT NO. : 4,700,294

DATED : October 13, 1987

INVENTOR(S) : John L. Haynes

It is certified that error appears in the above-identified patent and that said Letters Patent is hereby corrected as shown below:

Abstract, Line 6, change "multivalues" to --multivalued--.

Column 1, Line 47, change "useof" to --use of--.

Column 1, Line 51, change "counter" to --counted--.

Column 1, Line 64, change "with" to --which--.

Column 3, Line 21, after "invention" insert --;--.

Column 3, Line 66, change "decompacton" to --decompaction--.

Column 6, Line 42, change "a" to --as--.

Column 6, Line 44, change "acumulating" to --accumulating--.

Column 7, Line 18, after "FIG. 3A," do not start a paragraph.

Column 7, Line 51, after "inputs" insert --,-- (comma).

Column 8, Line 9, change "for" to --from--.

Column 9, Line 13, change "nad" to --and--.

Column 9, Line 31, change "Z" (capital) to --z-- (small).

Column 9, Line 45, after "stack" insert --,-- (comma).

Column 9, Line 59, change "PRT1" to --PTR1--.

Column 9, Line 60, change "520" to --530--.

Column 10, Line 5, change "PRT2" to --PTR2--.

Column 10, Line 55, change "with" to --within--.

Column 11, Line 21, change "W" (capital) to --w-- (small).

Column 11, Line 24, change "Y" (capital) to --y-- (small).

UNITED STATES PATENT AND TRADEMARK OFFICE
CERTIFICATE OF CORRECTION

PATENT NO. : 4,700,294
DATED : October 13, 1987
INVENTOR(S) : John L. Haynes

It is certified that error appears in the above-identified patent and that said Letters Patent is hereby corrected as shown below:

Column 12, Line 25, change "commercial" to --commercially--.
Column 13, Line 3, after "value" insert --is--.
Column 13, Line 54, change "equal" to --equals--.
Column 14, Line 48, after "not" insert --to--.
Column 14, Line 63, after "of" do not start a paragraph.
Column 14, Line 66, after "the" insert --N--.
Column 14, Line 66, after "all" delete "N".
Column 15, Line 7, after "number" insert --,-- (comma).
Column 15, Line 14, change "a" (second occurrence) to --at--.
Column 16, Line 11, change "compaction decompaction" to --compaction-decompaction--.
Column 17, Line 58, delete "word".
Column 18, Line 2, change "signed" to --assigned--.
Column 18, Line 65, change "said" to --set--.
Column 19, Line 2, change "said" to --set--.
Column 19, Line 3, change "said" to --set--.
Column 19, Line 17, change "said" to --set--.
Column 19, Line 18, change "said" to --set--.
Column 19, Line 40, change "said" to --set--.
Column 19, Line 57, change "said" to --is set--.
Column 20, Line 9, change "then" to --the--.

UNITED STATES PATENT AND TRADEMARK OFFICE
CERTIFICATE OF CORRECTION

PATENT NO. : 4,700,294

DATED : October 13, 1987

INVENTOR(S) : John L. Haynes

It is certified that error appears in the above-identified patent and that said Letters Patent is hereby corrected as shown below:

Column 20, Line 10, change "the" to --then--.

Column 20, Line 40, after "2740" insert --)-- (close parenthesis).

Column 20, Line 65, after "in" do not start a paragraph.

Column 21, Line 4, change "said" to --set--.

Column 21, Line 9, change "said" to --set--.

Column 21, Line 11, change "in" to --is--.

Column 21, Line 52, change "595" to --596--.

Column 21, Line 64, after "a" do not start a paragraph.

Column 21, Lines 67-68, change "flurescent" to --fluorescent--.

Column 22, Line 31, before "and the" delete "and".

Column 23, Line 14, change "or" to --more--.

Column 23, Line 26, after "liquid," do not start a paragraph.

Column 23, Line 65, change "signal" to --signals--.

Column 23, Line 67, change "signal" to --signals--.

UNITED STATES PATENT AND TRADEMARK OFFICE
CERTIFICATE OF CORRECTION

PATENT NO. : 4,700,294

DATED : October 13, 1987

INVENTOR(S) : John L. Haynes

It is certified that error appears in the above-identified patent and that said Letters Patent is hereby corrected as shown below:

Column 26, Line 14, after "number" insert --of--.

Column 27, Line 21, delete "an".

Column 27, Line 61, change "signal" to --signals--.

Column 29, Line 2, change "associately" to --associatively--.

Column 29, Line 6, change "parameters" to --parameter--.

Signed and Sealed this

Seventeenth Day of May, 1988

Attest:

DONALD J. QUIGG

Attesting Officer

Commissioner of Patents and Trademarks